(12) United States Patent
Frank-Kamenetskii et al.

(10) Patent No.: US 6,596,486 B2
(45) Date of Patent: *Jul. 22, 2003

(54) METHODS AND COMPOSITIONS PERTAINING TO PD-LOOPS

(75) Inventors: Maxim D. Frank-Kamenetskii, Brookline; Nikolay O. Bukanov, Framingham; Vadim V. Demidov; Heiko Kuhn, both of Boston; Natalia E. Broude, Natick, all of MA (US)

(73) Assignee: Trustees of Boston University, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/758,735

(22) Filed: Jan. 11, 2001

(65) Prior Publication Data

US 2001/0010915 A1 Aug. 2, 2001

Related U.S. Application Data

(63) Continuation of application No. 09/302,201, filed on Apr. 29, 1999, now Pat. No. 6,265,166.
(60) Provisional application No. 60/083,684, filed on Apr. 29, 1998.

(51) Int. Cl.[7] .................................................. C12Q 1/68
(52) U.S. Cl. .......................... 435/6; 536/23.3; 536/26.1
(58) Field of Search ............................ 435/6; 536/233, 536/26.6

(56) References Cited

U.S. PATENT DOCUMENTS 5,837,459 A    11/1998  Berg et al. .................... 435/6
6,265,166 B1 *  7/2001  Frank-Kamentskii et al. .. 435/6

FOREIGN PATENT DOCUMENTS

| EP | 0756009 | 1/1997 |
| WO | WO 95/08556 | 3/1995 |
| WO | WO 96/02558 | 2/1996 |

OTHER PUBLICATIONS

Almarsson et al., Proc. Natl. Acad. Sci., 90:7518–22, Aug. 1993.*

Almarsson, O. et al, Molecular mechanics calculations of the structures of polyamide nucleic acid DNA duplexes and triple helical hybrids. *Proc. Natl. Acad. Sci. USA 90*, 7518–7522 (1993).

(List continued on next page.)

*Primary Examiner*—W. Gary Jones
*Assistant Examiner*—Juliet Einsmann
(74) *Attorney, Agent, or Firm*—Brian D. Gildea

(57) ABSTRACT

A stable complex, we refer to as a PD-Loop, between double stranded nucleic acid and a nucleobase polymer is assembled with the aid of strand invading peptide nucleic acid (PNA). The PD-Loop can be used in the detection, analysis, quantitation and even in the affinity capture of the duplex nucleic acid. Alternatively, the PD-Loop can be used to initiate polymerase extension of a primer to thereby facilitate sequencing of the double stranded nucleic acid even in the presence of large excesses of unrelated double stranded nucleic acid. As an additional feature, the PD-Loop can also be used to generate a construct comprised of a double stranded nucleic acid through which is threaded a single stranded dosed circular nucleic acid wherein the closed circular nucleic acid can be used in a signal amplification methodology.

24 Claims, 7 Drawing Sheets

OTHER PUBLICATIONS

Banér, J. et al., Signal amplification of padlock probes by rolling circle replication. *Nucl. Acids Res.* 26, 5073–5078 (1998).

Bukanov, N. O. et al, PD–loop: a complex of duplex DNA with an oligonucleotide. *Proc. Natl. Acad. Sci. USA* 95, 5516–5520 (1998).

Demidov, V. V. et al, Electron microscopy mapping of oligopurine tracts in duplex DNA by peptide nucleic acid targeting. *Nucl. Acids. Res.* 22, 5218–5222 (1994).

Demidov, V. V. et al, Kinetic analysis of specificity of duplex DNA targeting by homopyrimidine peptide nucleic acids, *Biophy. Journal* 72, 2763–2769 (1997).

Demidov, V. V. et al, Kinetics and mechanism of polymide ("peptide") nucleic acid binding to duplex DNA. *Proc. Natl, Acad. Sci USA* 92, 2637–2641 (1995).

Fire, A. et al, Rolling replication of short DNA circles. *Proc. Natl. Acad. Sci. USA* 92, 4641–4645 (1995).

Footer, M. et al, Biochemical evidence that a D–loop is part of a four–stranded PNA–DNA bundle. Nicke–mediated cleavage of duplex DNA by a Gly–Gly–His–Bis–PNA. *Biochem.* 35, 10673–10679 (1996).

Frank–Kamenetskii, M.D. et al, Triplex DNA Structures. *Annu. Rev. Biochem.* 64, 64–95 (1995).

Frank–Kamenetskii, M.D., DNA topology. *J Molecular Structure (Theocom)* 336, 235–243 (1995).

Fu, D.–J. et al, Sequencing double–stranded DNA by strand displacement. *Nucl. Acids Res.* 25, 677–679 (1997).

Fujiwara, J. et al, Direct probing: covalent attachment of probe DNA to double–stranded target DNA. *Nucleic Acids Res.* 26, 5728–5733 (1998).

Heiner, C. R. et al, Sequencing Multimegabase–Template DNA with BigDye Terminator Chemistry. *Genome Research* 8, 557–561 (1998).

Ito, T. et al, Sequence–specific DNA purification by triplex affinity capture. *Proc. Natl. Acad. Sci. USA* 89, 275–283 (1996).

Karapetian, A. T. et al, Theoretical treatment of melting of complexing of DNA with ligands having several types of binding sites on helical and single–stranded DNA. *J. Biomol. Struc. & Dynamics* 14, 275–283 (1996).

Kuhn, H. et al, An experimental study of mechanism and specificity of Peptide Nucleic Acid (PNA) binding to duplex DNA, *J. Mol. Biol.* 286, 1337–1345 (1999).

Kuhn, H.et al, Kinetic sequence discrimination of cationic bis PNAs upon targeting of double–stranded DNA. *Nucl. Acids. Res.* 26582–587 (1998).

Kuhn, H. et al, Topological links between duplex DNA and a circular DNA single strand. *Angew. Chem. Int. Ed.* 38, 1446–1449 (1999).

Kurakin, A. et al, Cooperative strand displacement by peptide nucleic acid (PNA) *Chem. & Biol.* 5, 81–89 (1998).

Kutyavin, I.V. et al, Oligonucleotides Containing 2–Aminoadenine and 2–Thiiothymine Acts as Selectivity Binding Complementary Agents. *Biochem.* 35, 11170–11176 (1996).

Lizardi, P. M. et al, Mutation detection and single–molecule counting using isothermal rolling–circle amplification. *Nature Genetics* 19, 225–232 (1998).

Lomakian, A. et al, A theoretical analysis of specificity of nucleic acid interactions with olignucleotides and Peptide Nucleic Acids (PNAs). *J. Mol. Biol.* 276, 57–70 (1998).

Malik, A.N., Direct sequencing of inserts cloned into lambda vectors. *Methods in Mol. Bio., vol. 23: DNA Sequencing Protocols* 141–148 (1993).

Malkov, V. A. et al, RecA Protein Assisted Selection Reveals a Low Fidelity of Recognition of Homology in a Duplec DNA by an Oligonucleotide. *J. Mol. Biol.* 271, 168–177 (1997).

Møllegaard, N.E. et al., Peptide nucleic acid DNA strand displacement loops as article transcription promoters. *Proc. Natl. Acad. Sci. USA* 91, 3892–3895 (1994).

Nielsen, P. E. et al., Evidence for $(PNA)_2$/DNA triplex structure upon binding of PNA to dsDNA by strand displacement. *J. Mol. Recogn.* 7, 165–170 (1994).

Niemeyer, C.M., DNA as a Material for Nanotechnology. *Angew. Chem. Int. Ed. Engl.* 36, 585–587 (1997).

Nilsson, M. et al, Padlock probes reveal single–nucleotide differences, parent of origin and in situ distribution of centromeric sequences in human chromosomes 13 and 21. *Nature Genetics* 16, 252–255 (1997).

Nilsson, M. et al, Padlock Probes: Circulating Oligonucleotides for Localized DNA Detection. *Science* 265, 2085–2088 (1994).

Perry–O'Keefe, H. et al, Peptide nucleic acid pre–gel hybridization: An alternative to Southern hybridization. *Proc. Natl. Acad. Sci. USA* 93, 14670–14675 (1996).

Potaman, V. N. et al, Overcoming a barrier for DNA polymerization in triplex–forming sequences. *Nucl. Acids Res.* 27, e5 (1999).

Ryan, K. et al, Triplex–directed self–assembly of an artificial sliding clamp on duplex DNA. *Chem. & Biol.* 5, 59–67 (1998).

Sanger, F. et al, DNA seqeuncing with chain–terminating inhibitors. *Proc. Natl. Acad. Sci. USA* 74, 5463–5467 (1977).

Schluep, T. et al., Purification of plasmids by triplex affinity interaction. *Nucl. Acids. Res.* 26, 4524–4528 (1998).

Seeman, N. C., DNA Components for Molecular Architecture. *Acc. Chem. Res.* 30, 357–363 (1997).

Seeman, N. C., DNA nanotechnology: Novel DNA Constructions. *Annu. Rev. Biophy. Biomol. Struct.* 27, 225–248 (1998).

Seeman, N. C., Nucleic Acid Nanostructure and Topology. *Angew. Chem. Int. Ed.* 37, 3220–3238 (1998).

Shepard, A.R. et al, Magnetic bead capture of cDNAs from double–stranded plasmid cDNA libraries. *Nucl. Acids Res.* 25, 3183–3185 (1997).

Smulevitch. S. V. et al, Enhancement of strand invasion by oligonucleotides through manipulation of backbone charge. *Nature Biotech.* 14, 1700–1704 (1996).

Southern, E.D. et al, Detection of specific sequences among DNA fragments separated by gel electrophoresis. *J. Mol. Bio.* 98, 503–517 (1975).

Thomas, M. et al, Hybridization of RNA to double–stranded DNA: Formation of R–loops. *Proc. Natl. Acad. Sci. USA* 73, 2294–2298 (1976).

West, S. C., Enzymes and Molecular Mechanisms of Genetic Recombination. *Annu. Rev. Biochem.* 61603–640 (1992).

Wetmur, J. G., DNA Probes: Applications of the Principals of Nucleic Acid Hybridization. *Critical Reviews in Biochem. And Mol. Bio.* 26, 227–259 (1991).

Zhang, D. Y. et al, Amplification of target–specific, ligation–dependent circular probe. *Gene 211*, 277–285 (1998).

Cherney, D. I. et al, Electron Microscopic Studies of Sequence–Specific Recognition of Duplex DNA by Different Ligands. *Journal of Molecular Recognition 7*, 171–176 (1994).

Demidov, V. V. et al, Complexes of Duplex DNA with Homopyrimidine Peptide Nucleic Acid (PNA). *J. Biomolec. Struct. Dyn. 12*, A042 (1995).

Demidov, V. V. et al, Sequence selective double strand DNA cleavage by Peptide Nucleic Acid (PNA) targeting using nuclease S1. *Nucleic Acids Research 21*, 2103–2107 (1993).

Frank–Kamenetskii, M.D. et al, Triplex DNA Structures. *Annu. Rev. Biochem. 64*, 65–95 (1995).

* cited by examiner

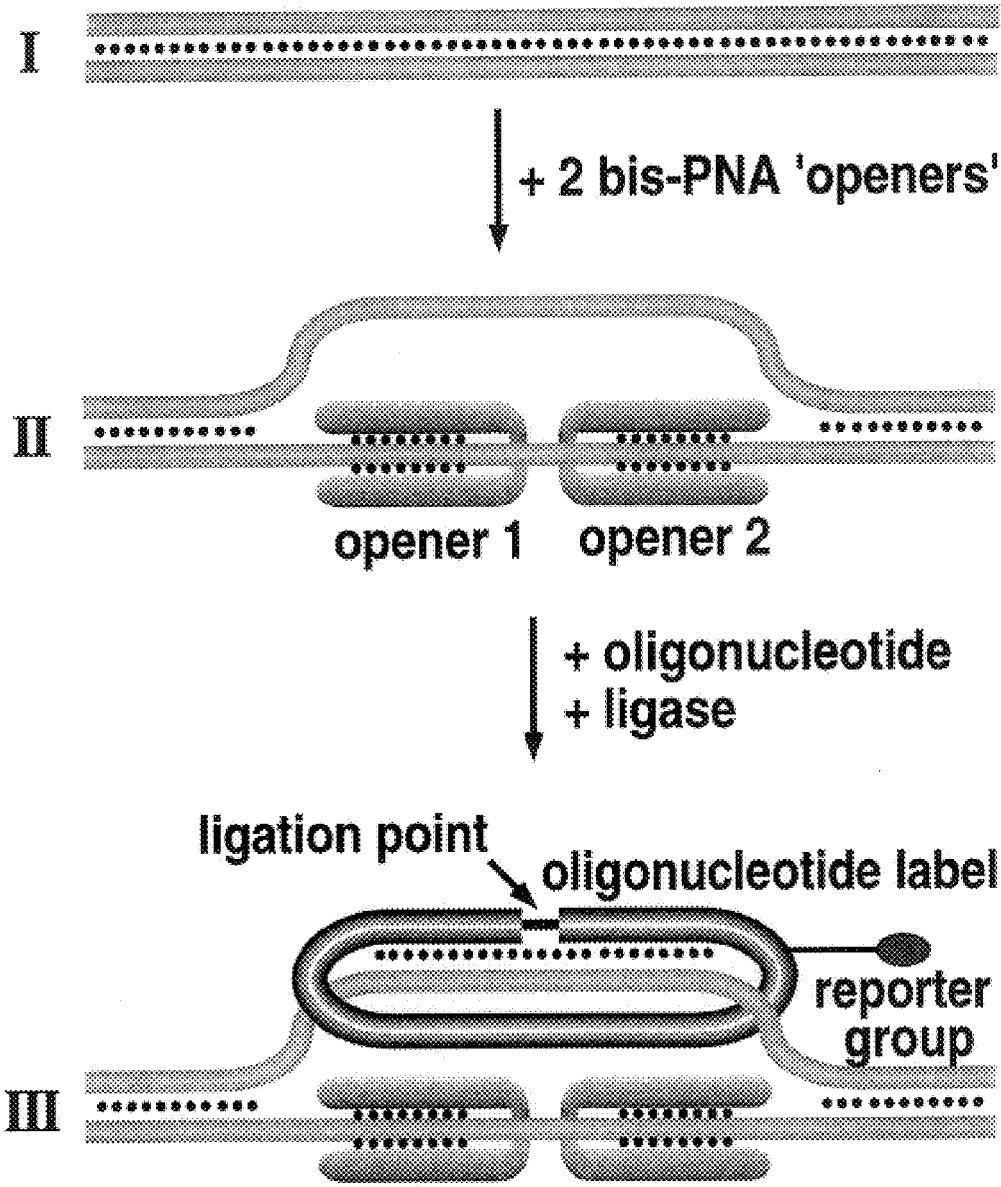

Templates:
Figure 11a
Earring Tag Complex
Figure 11b
Circular Oligonucleotide
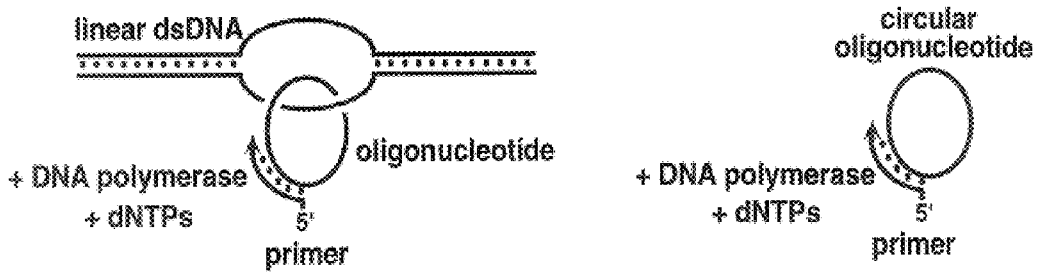
Figure 11c
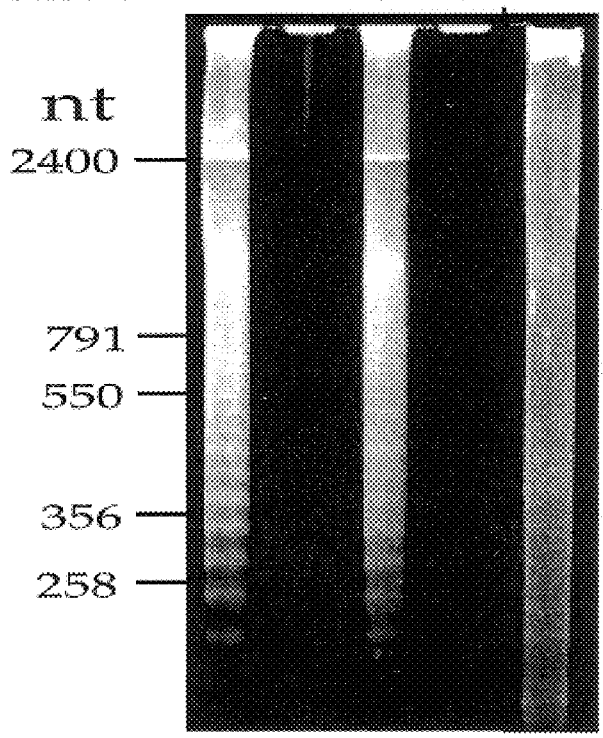

```
                               SEQUENCE LISTING

<160> NUMBER OF SEQ ID NOS: 18

<210> SEQ ID NO 1

<211> LENGTH: 13
<212> TYPE: DNA
<213> ORGANISM: Artificial Sequence
<220> FEATURE:
<221> NAME/KEY: misc_feature
<222> LOCATION: (13)
<223> OTHER INFORMATION: 3' biotin
<223> OTHER INFORMATION: Description of Artificial Sequence: Labeled
      Synthetic Oligonucletide

<400> SEQUENCE: 1
gaaggttcga agg                                                        13

<210> SEQ ID NO 2

<211> LENGTH: 11
<212> TYPE: DNA
<213> ORGANISM: Artificial Sequence
<220> FEATURE:
<221> NAME/KEY: misc_feature
<222> LOCATION: (11)
<223> OTHER INFORMATION: 3' biotin
<223> OTHER INFORMATION: Description of Artificial Sequence: Labeled
      Synthetic Oligonucletide

<400> SEQUENCE: 2
aaggttcgaa g                                                          11

<210> SEQ ID NO 3

<211> LENGTH: 14
<212> TYPE: DNA
<213> ORGANISM: Artificial Sequence
<220> FEATURE:
<221> NAME/KEY: misc_feature
<222> LOCATION: (1)
<223> OTHER INFORMATION: 5' biotin
<223> OTHER INFORMATION: Description of Artificial Sequence: Labeled
      Synthetic Oligonucletide

<400> SEQUENCE: 3
gaaggctgga agga                                                       14

<210> SEQ ID NO 4

<211> LENGTH: 19
<212> TYPE: DNA
<213> ORGANISM: Artificial Sequence
<220> FEATURE:
<223> OTHER INFORMATION: Description of Artificial Sequence: One Strand
      of a plasmid

<400> SEQUENCE: 4 tcccttcga accttcttt                                                   19

<210> SEQ ID NO 5
```

<211> LENGTH: 19
<212> TYPE: DNA
<213> ORGANISM: Artificial Sequence
<220> FEATURE:
<223> OTHER INFORMATION: Description of Artificial Sequence: One Strand
      of a plasmid

<400> SEQUENCE: 5
aaagaaggtt cgaagggga                                                  19

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: One Strand
      of a plasmid

<400> SEQUENCE: 6
tccccttcct tcgaaccttc cttcttt                                         27

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: One Strand
      of a plasmid

<400> SEQUENCE: 7
aaagaaggaa ggttcgaagg aagggga                                         27

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 8
tctccagcct ctcaccgcat                                                 20

<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 9
taatgcggtg a                                                          11

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: One Strand
      of a Plasmid

<400> SEQUENCE: 10
tttccttcca gccttcttt                                     19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: One Strand
      of a Plasmid

<400> SEQUENCE: 11
aaagaaggct ggaaggaaa                                     19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucletide

<400> SEQUENCE: 12
tctccagcct ctcaccgcat                                    20

<210> SEQ ID NO 13
<211> LENGTH: 15
<212> TYPE: DNA
<213> ORGANISM: Artificial Sequence
<220> FEATURE:
<221> NAME/KEY: misc_feature
<222> LOCATION: (1)
<223> OTHER INFORMATION: 5' fluorescein
<223> OTHER INFORMATION: Description of Artificial Sequence: Labeled
      Synthetic Oligonucletide

<400> SEQUENCE: 13
aagaaggttc gaagg                                         15

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 14
agaggaagct actggaggag a                                  21

<210> SEQ ID NO 15
<211> LENGTH: 13
<212> TYPE: DNA
<213> ORGANISM: Artificial Sequence
<220> FEATURE:
<221> NAME/KEY: misc_feature
<222> LOCATION: (1)
<223> OTHER INFORMATION: 5' fluorescein
<223> OTHER INFORMATION: Description of Artificial Sequence: Labeled
      Synthetic Oligonucletide

<400> SEQUENCE: 15
gaagctactg gag                                           13

```
<210> SEQ ID NO 16

<211> LENGTH: 44
<212> TYPE: DNA
<213> ORGANISM: Artificial Sequence
<220> FEATURE:
<221> NAME/KEY: misc_feature
<222> LOCATION: (18)..(19)
<223> OTHER INFORMATION: biotin label
<223> OTHER INFORMATION: Description of Artificial Sequence: Synthetic
      Oligonucleotide

<400> SEQUENCE: 16
ctggaggaga ttttgtggta tcgattcgtc tcttgaggaa gcta                    44

<210> SEQ ID NO 17

<211> LENGTH: 16
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 17
gacgaatcga taccac                                                   16

<210> SEQ ID NO 18

<211> LENGTH: 13
<212> TYPE: DNA
<213> ORGANISM: Artificial Sequence
<220> FEATURE:
<223> OTHER INFORMATION: Description of Artificial Sequence: DNA primer

<400> SEQUENCE: 18
gaaggttcga agg                                                      13
```

METHODS AND COMPOSITIONS PERTAINING TO PD-LOOPS

CROSS REFERENCE TO RELATED APPLICATIONS

This application is a continuation of U.S. patent application No. 09/302,201 filed on Apr. 29, 1999 (now U.S. Pat. No. 6,265,166). This application also claims the benefit of U.S. Provisional Application No. 60/083,684 filed on Apr. 29, 1998.

STATEMENT REGARDING FEDERALLY SPONSORED RESEARCH OR DEVELOPMENT

The U.S. Government has certain rights in this invention as provided for by the terms of Grant Nos. GM 52201 and GM 54434 awarded by the National Institute of Health.

BACKGROUND OF THE INVENTION

1. Field of the Invention

This invention relates to the methods and compositions suitable for the detection, analysis, quantitation and sequencing of double stranded nucleic acids 2. Description of the Related Art A. Invasion of double stranded nucleic acid Linear, non-supercoiled double-stranded DNA (dsDNA) is known to be able to accommodate an additional oligonucleotide strand with much less efficiency as compared with single-stranded nucleic adds and supercoiled DNAs. Formation of intermolecular triplexes is mostly limited to long homopurine-homopyrimidine regions (See: Frank-Kamenetskii, M. D., & Mirkin, S. M. (1995) *Annu. Rev. Biochem.* 64, 65–95 and Soyfer, V. N. & Potaman, V. N. (1996) *Triple-Helical Nucleic Acids* (Springer, New York). D-loops are formed in linear dsDNA only at the ends of the DNA duplex and when using long single-stranded DNA molecules (See: Wetmur, J. G. (1991) *Critical Rev. Biochem. Mol. Biol.* 26, 227–259). R-loops may be formed inside linear dsDNA, but long RNAs and transient DNA denaturation is required (See: Thomas, M., White, R. L., & Davis, R. W. (1976) *Proc. Natl. Acad. Sci. USA* 73, 2294–2298). A complex between an oligodeoxynucleotide (ODN) and linear dsDNA can be formed with the assistance of the RecA protein. However, the fidelity of recognition of this complex is lower as compared with the protein-free DNA—DNA. Moreover, the complex is unstable upon deproteinization (See: West, S. C. (1992) *Annu. Rev. Biochem.* 61, 603–640 and Malkov, V. A., Sastry, L. & Camerini-Otero, R. D. (1997) *J. Mol. Biol.* 271, 168–177). It has recently been demonstrated that a pair of complementary modified ODNs will bind to dsDNA as a result of their self-mediated invasion of the DNA duplex. However, these complexes were formed only at the ends of linear dsDNA (See: Kutyavin, I. V., Rhinehart, R. L., Lukhtanov, E. A., Gorn, V. V., Meyer, R. B., Jr., & Gamper, H. B., Jr. (1996) *Biochemistry* 35, 11170–11176). In addition, a few techniques exist for the formation of specific complexes between ODNs and dsDNA based upon either prior DNA denaturation or degradation of one DNA strand before ODN binding. These techniques, however, require subsequent reconstruction or reparation of the DNA duplex (See: Shepard, A. R., & Rae, J. L. (1997) *Nucleic Acid Res.* 25, 3183–3185 and Anonymous (1997/1998) in *Gibco BRL Products & Reference Guide,* (Life Technologies, Gaithersburg, Md.), pp. 1914–1915).

B. Sequencing Double Stranded Nucleic Acids

Progress in enzymatic (or dideoxy) DNA sequencing has (See: Sanger, F., Nicklen, S. and Coulson, A. R. (1977) *Proc. Natl. Acad. Sci. USA* 74, 5463–5467) completely changed the science of molecular genetics and revolutionized the field of modern biotechnology. However, the development of improved dideoxy sequencing methodologies as well as the introduction of new sequencing approaches promises to further facilitate great advancements in science.

High quality sequence data is generally obtained using dideoxy sequencing reactions on purified single-stranded (ss) DNA templates. Consequently, Sanger sequence typically requires the performance of laborious ssDNA isolation (See: Griffin, H. G. and Griffin, A. M., eds. (1993) *DNA Sequencing Protocols.* Humana Press, Totowa, N.J., USA, Brown, T. A. (1994) *DNA Sequencing: The Basics.* IRL Press, Oxford, GB and Ansorge, W., Voss, H. and Zimmermann, J., eds. (1997) *DNA Sequencing Strategies: Automated and Advanced Approaches.* Wiley, New York, N.Y., US). To avoid ssDNA isolation, direct sequencing of double-stranded (ds) DNA was developed. However, the robustness of direct sequencing denatured dsDNA is often compromised by poor sequence readability and/or spurious sequence data resulting from non-specific mispriming. For this reason, isothermal dideoxy sequencing of dsDNA is normally limited to constructs of less than 50 kb. Thermal cycle sequencing overcomes this size limitation thereby allowing multimegabase-template dsDNA to be directly sequenced (See: Heiner, C. R., Hunkapiller, K L., Chen, S. -M., Glass, J. I. and Chen, E. Y. (1998) *Genome Res.* 8, 557–561). However, careful choice of various parameters and operation with the thermal cycler is requisite for cycle sequencing.

Therefore, it is highly desirable to develop isothermal methods for sequencing non-denatured dsDNA. To this end, solid phase sequencing of dsDNA restriction fragments by strand displacement or nick translation was recently described (See: Fu, D. -J., Köster, H., Smith, C. L. and Cantor, C. R. (1997) *Nucleic Acids Res.* 25, 677–679). Still, this approach cannot be applied for direct sequencing of long DNA or closed circular dsDNA.

C. Nucleic Acid Comprising Topologically Linked Structures

DNA is well known to adopt various topological (and pseudotopological) structures like knots, catenanes, Borromean rings and pseudorotaxanes. (See: M. D. Frank-Kamenetskii, *J. Mol. Struct.* (*Theochem*) 1995, 336, 235–243; N. C. Seeman, *Annu. Rev. Biophys. Biomol. Struct.* 1998, 27, 225–248; K. Ryan, E. T. Kool, *Chem. & Biol.* 1998, 5, 59–67; N. C. Seeman, *Angew. Chem.* 1998, 110, 3408–3428; and *Angew. Chem. Int. Ed. Engl.* 1998, 37, 3220–3238). It has long been recognized that DNA topology plays a crucial role in such fundamental biological phenomena as DNA supercoiling and topoisomerization (See M. D. Frank-Kamenetskii, *Unraveling DNA: The most important molecule of life,* Addison-Wesley, Reading, Mass., USA 1997, p. 214; and R. Sinden, *DNA Structure and Function,* Academic Press, San Diego, Calif., USA 1994, p. 398). Another reason for a considerable interest in higher order DNA topology structures stems from the realization that DNA topological and pseudotopological forms may provide stable and sequence-specific targeting of DNA. Accordingly, highly localized DNA detection and precise spatial positioning of various ligands on DNA scaffold becomes possible. This may lead to new applications in molecular biotechnology, gene therapy and in the emerging field of DNA nanotechnology (See: N. C. Seeman, *Acc. Chem. Res.* 1997, 30, 357–363; b) C. M. Niemeyer, *Angew. Chem.* 1997, 109, 603–606; and *Angew. Chem. Int. Ed. Engl.* 1997, 36, 585–587).

One of promising DNA pseudotopological constructions is the DNA padlock consisting of a long single-stranded (ss) DNA molecule forming a pseudorotaxane with a short cyclic oligodeoxynucleotide (cODN) (See: M. Nilsson, H. Malmgren, M. Samiotaki, M. Kwiatkowski, B. P. Chowdhary, U. Landegren, *Science* 1994, 265, 2085–2088; M. Nilsson, K. Krejci, J. Koch, M. Kwiatkowski, P. Gustavsson, U. Landegren, *Nature Gen.* 1997, 16, 252–254; P. M. Lizardi, X. Huang, Z. Zhu, P. Bray-Ward, D. C. Thomas, D. C. Ward, *Nature Gen.* 1998, 19, 225–232; and J. Banér, M. Nilsson, M. Mendel-Hartvig, U. Landegren, *Nucleic Acids Res.* 1998, 26, 5073–5078). Another interesting pseudorotaxane-type structure is the sliding clamp which contains a short cODN threaded on double-stranded (ds) DNA (See: K. Ryan, E. T. Kool, *Chem. & Biol.* 1998,5, 59–67, d) N. C. Seeman, *Angew. Chem.* 1998, 110, 3408–3428). Notwithstanding the value of the indicated pseudotopological structures for DNA labeling, note that in these constructions the cODN tag is allowed to slide along the target for considerable distances thereby compromising the precision of spatial positioning of the label.

SUMMARY OF THE INVENTION

Generally this invention relates to methods and compositions pertaining to PD-Loops. In one embodiment, this invention relates to a composition comprising a double stranded nucleic acid having at least one homopurine site and one or more PNA oligomers (at times the PNA oligomers will be referred to herein as "openers") which hybridize to the one or more homopurine sites to thereby create an extended open region inside the double stranded nucleic acid. To the extended open region of the double stranded nucleic acid is then hybridized a nucleobase polymer. The resulting novel composition is a PD-Loop.

In another embodiment, this invention relates to a method for hybridizing a nucleobase polymer to a double stranded nucleic acid to thereby form a PD-Loop. According to the method, a double stranded nucleic add comprising at least one homopurine site is chosen. To the one or more homopurine sites are then hybridized one or more PNA oligomers to thereby create an extended open region inside the double stranded nucleic acid. To this extended open region is hybridized a nucleobase polymer. This method for hybridizing a nucleobase polymer to a double stranded nucleic acid is unique and useful since the duplex need not be chemically or thermally denatured.

In another embodiment of this invention, the PD-Loop can be used to generate Sanger sequence ladders suitable for sequence analysis of the double stranded nucleic acid. In this embodiment, the nucleobase probe is a primer. According to the method, the PD-Loop is formed as previously described and then primer extension is initiated under suitable Sanger sequencing conditions. Under isothermal conditions, this process generates Sanger sequencing ladders from the double stranded nucleic acid template. The Sanger sequencing ladders can then be analyzed by conventional techniques to thereby determine the sequence of the double stranded nucleic add. The method can be repeated until no more suitable homopurine sites are found which would allow one to form a PD-Loop, until the entire sequence of the double stranded template is determined or until the desired sequence information is obtained.

In still another embodiment, this invention pertains to a Sanger sequence ladder which is generated isothermally from a double stranded nucleic acid without the application of chemical or thermal denaturing conditions.

In still another embodiment, this invention is related to a double stranded nucleic acid having a linked single stranded closed circular nucleic acid wherein the single stranded nucleic acid is threaded through the strands of the duplex. This construct will at times be referred to herein as the "Earring".

The invention further relates to a method of forming a double stranded nucleic acid having a linked single stranded closed circular nucleic acid wherein the single stranded nucleic acid is threaded through the strands of the duplex. According to the method, the double stranded nucleic acid is invaded to thereby create an extended open region inside the double stranded nucleic acid. To the extended open region is then hybridized an oligonucleotide in such a way that the two termini of the oligonucleotide are complementary to the exposed double stranded nucleic acid and are juxtapositioned to one strand of the double stranded nucleic acid. Once this PD-Loop is formed, the two termini of the oligonucleotide are then ligated to thereby form the single stranded closed circular nucleic acid. Preferably, the termini are ligated using a ligase but optionally the termini can be ligated using chemical methodology.

In yet another embodiment, the single stranded closed circular nucleic acid is used in a signal amplification methodology. According to the method, a primer is hybridized to the single stranded closed circular nucleic acid. A polymerase dependent primer extension reaction is then initiated to thereby generate one or more single stranded copies of the single stranded dosed circular nucleic acid. Preferably, numerous copies of the single stranded closed circular nucleic acid will be produced such that it results in efficient signal amplification by the detection of the copy or copies. In the most preferred embodiment, a hybridization site for a reporter probe is repeated numerous times per generated copy of the single stranded closed circular nucleic acid.

BRIEF DESCRIPTION OF THE DRAWINGS

FIG. 8 is an illustration of the formation of a PD-Loop "Earring".

FIGS. 11A and 11B are illustrations of an "Earring" used in primer dependent signal amplification.

FIG. 11C is an image of a gel containing experimental data.

DESCRIPTION OF THE PREFERRED EMBODIMENTS

Figure 1:
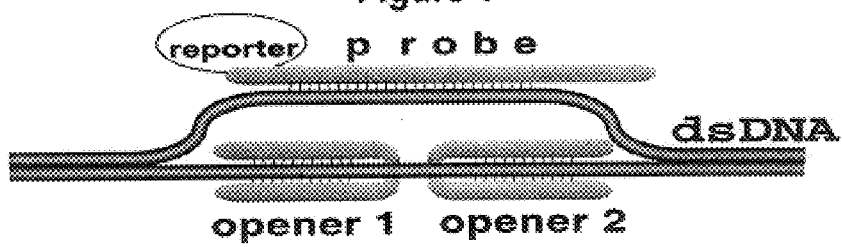
FIG. 1 is an illustration of an exemplary PD-Loop

1. Definitions:
   a. As used herein, the term "nucleobase" shall include those naturally occurring and those non-naturally occurring heterocyclic moieties commonly known to those who utilize nucleic acid technology or utilize peptide nucleic acid technology to thereby generate polymers which can sequence specifically bind to nucleic acids.
   b. As used herein, the term "nucleobase sequence" or "nucleobase sequences" shall mean any segment of a polymer which comprises nucleobase containing subunits. Non-limiting examples of suitable polymers or polymers segments include oligodeoxynucleotides, oligoribonucleotides, peptide nucleic acids, nucleic acid analogs, nucleic acid mimics or chimeras.
   c. As used herein the term "nucleobase polymer" shall mean a polymer comprising a nucleobase sequence or nucleobase sequences. Non-limiting examples of nucleobase polymers are selected from the group consisting of oligodeoxynucleotides, oligoribonucleotides, peptide nucleic acids, nucleic acid analogs, nucleic acid mimics or chimeras.
   d. As used herein, the term "peptide nucleic acid" or "PNA" shall be defined as any oligomer, linked polymer or chimeric oligomer, comprising two or more PNA subunits (residues), including any of the compounds referred to or claimed as peptide nucleic acids in U.S. Pat. Nos. 5,539,082, 5,527,675, 5,623,049, 5,714,331, 5,736,336, 5,773,571 or 5,786,461 (all of which are herein incorporated by reference). The term "peptide nucleic acid" or "PNA" shall also apply to polymers comprising two or more subunits of those nucleic acid mimics described in the following publications: Diderichsen et al., *Tett. Lett.* 37: 475478 (1996); Fujii et al., *Bioorg. Med. Chem. Lett.* 7: 637-627 (1997); Jordan et al., *Bioorg. Med. Chem. Lett.* 7: 687–690 (1997); Krotz et al., *Tett. Lett.* 36: 6941–6944 (1995); Lagriffoul et al., *Bioorg. Med. Chem. Lett.* 4: 1081–1082 (1994); Lowe et al., *J. Chem. Soc. Perkin Trans.* 1, (1997) 1: 539–546; Lowe et al., *J. Chem. Soc. Perkin Trans.* 11:547–554 (1997); Lowe et al., *J. Chem. Soc. Perkin Trans.* 11:555–560 (1997); Petersen et al., *Bioorg. Med. Chem. Lett.* 6: 793–796 (1996); Diederichsen, U., *Bioorganic & Med. Chem. Lett.,* 8: 165–168 (1998); Cantin et al., *Tett. Lett.,* 38: 4211–4214 (1997); Ciapetti et al., *Tetrathedron,* 53: 1167–1176 (1997) and Lagriffoule et al., *Chem. Eur. J.,* 3: 912–919 (1997).

In preferred embodiments, a PNA is a polymer comprising two or more subunits of the formula:

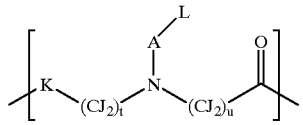

wherein, each J is the same or different and is selected from the group consisting of H, $R^1$, $OR^1$, $SR^1$, $NHR^1$, $NR^1_2$, F, Cl, Br and I. Each K is the same or different and is selected from the group consisting of O, S, NH and $NR^1$. Each $R^1$ is the same or different and is an alkyl group having one to five carbon atoms which may optionally contain a heteroatom or a substituted or unsubstituted aryl group. Each A is selected from the group consisting of a single bond, a group of the formula; —$(CJ_2)_s$— and a group of the formula; —$(CJ_2)_sC(O)$—, wherein, J is defined above and each s is an integer from one to five. The integer t is 1 or 2 and the integer u is 1 or 2. Each L is the same or different and is independently selected from the group consisting of J, adenine, cytosine, guanine, thymine, uridine, 5-methylcytosine, 2-aminopurine, 2-amino-chloropurine, 2,6-daminopurine, hypoxanthine, pseudoisocytosine, 2-thiouracil, 2-thiothymidine, other naturally occurring nucleobase analogs, other non-naturally occurring nucleobases, substituted and unsubstituted aromatic moieties, biotin, fluorescein and dabcyl. In the most preferred embodiment, a PNA subunit consists of a naturally occurring or non-naturally occurring nucleobase attached to the aza nitrogen of the N-[2-(aminoethyl)]glycine backbone through a methylene carbonyl linkage.

e. As used herein, the term "chimera" or "chimeric oligomer" shall mean a nucleobase polymer comprising two or more linked subunits which are selected from different classes of subunits. For example, a PNA/DNA chimera would comprise at least two PNA subunits linked to at least one 2'-deoxyribonucleic acid subunit (For exemplary methods and compositions related to PNA/DNA chimera preparation See: WO96/40709). Exemplary component subunits of the chimera are selected from the group consisting of PNA subunits, naturally occurring amino acid subunits, DNA subunits, RNA subunits and subunits of analogues or mimics of nucleic acids.
   f. As used herein, the term "linked polymer" shall mean a nucleobase polymer comprising two or more polymer segments or nucleobase sequences which are linked by a linker. Non-limiting examples of polymer segments or nucleobase sequences which are linked to form the linked polymer are selected from the group consisting of an oligodeoxynucleotide, an oligoribonucleotide, a peptide, a polyamide, a peptide nucleic acid (PNA) and a chimera.
   g. As used herein, the term "dark probe" shall be a nucleobase polymer which hybridizes to a hybridization site on a nucleobase polymer to thereby cause a detectable change in at least one physical property of at least one attached label to thereby detect or quantitate the presence of the hybridization site in a sample of interest. Non-limiting examples of dark probes include hairpin forming nucleic acid Molecular Beacons (See: Tyagi et al., Tyagi2 et al. and Tyagi3 et al.), PNA Molecular Beacons (See: U.S. Ser. No. 08/958,532 (abandoned) and copending U.S. Ser. No. 09/179,298, both incorporated herein by reference) as well as Linear Beacons (See: copending U.S. Ser. No. 09/179,162, herein incorporated by reference).
   h. As used herein, the terms "label" and "detectable moiety" shall be interchangeable and shall refer to moieties which can be attached to a nucleobase polymer to thereby render the probe or oligomer detectable by an instrument or method.

2. Detailed Description
   I. General:
   PNA Synthesis
   Methods for the chemical assembly of PNAs are well known (See: U.S. Pat. Nos. 5,539,082, 5,527,675, 5,623,049, 5,714,331, 5,736,336, 5,773,571 or 5,786,571, herein incorporated by reference). Chemicals and instrumentation for the support bound automated chemical assembly of Peptide Nucleic Acids are now commercially available.

Both labeled and unlabeled PNA oligomers are likewise available from commercial vendors of custom PNA oligomers. Chemical assembly of a PNA is analogous to solid phase peptide synthesis, wherein at each cycle of assembly the oligomer possesses a reactive alkyl amino terminus which is condensed with the next synthon to be added to the growing polymer. Because standard peptide chemistry is utilized, natural and non-natural amino acids are routinely incorporated into a PNA oligomer. Because a PNA is a polyamide, it has a C-terminus (carboxyl terminus) and an N-terminus (amino terminus). For the purposes of the design of a hybridization probe suitable for antiparallel binding to the target sequence (the preferred orientation), the N-terminus of the probing nucleobase sequence of the PNA probe is the equivalent of the 5'-hydroxyl terminus of an equivalent DNA or RNA oligonucleotide.

Nucleic Acid Synthesis and Labeling

Nucleic acid oligomer (oligonucleotide and oligoribonucleotide) synthesis has become routine. For a detailed description of nucleic acid synthesis please see Gait, M. J., *Oligonucleotide Synthesis: a Practical Approach*. IRL Press, Oxford England. Preferably, labeled and unlabeled nucleic acid oligomers are synthesized on supports in what is known as solid phase synthesis. Alternatively, they are synthesized in solution. Those of ordinary skill in the art will recognize that both labeled, unlabeled and/or modified oligonucleotides (DNA, RNA and synthetic analogues thereof) are readily available. They can be synthesized using commercially available instrumentation and reagents or they can be purchased from commercial vendors of custom manufactured oligonucleotides. Patents which discuss various compositions, supports and methodologies for the synthesis and labeling of nucleic acids include: U.S. Pat. Nos. 5,476,925, 5,453,496, 5,446,137, 5,419,966, 5,391,723, 5,391,667, 5,380,833, 5,348,868, 5,281,701, 5,278,302, 5,262,530, 5,243,038, 5,218,103, 5,204,456, 5,204,455, 5,198,527, 5,175,209, 5,164,491, 5,112,962, 5,071,974, 5,047,524, 4,980,460, 4,923,901, 4,786,724, 4,725,677, 4,659,774, 4,500,707, 4,458,066, and 4,415,732 which are herein incorporated by reference.

Labels

The labels attached to the nucleobase polymer used with this invention are generally available as amine reactive labeling reagents. Preferred labeling reagents will be supplied as carboxylic acids or as the N-hydroxysuccinidyl esters of carboxylic acids. Preferred fluorochromes (fluorophores) include 5(6)-carboxyfluorescein (Flu), 6-((7-amino-4-methylcoumarin-3-acetyl)amino)hexanoic acid (Cou), 5(and 6)-carboxy-X-rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.) or the Alexa dye series (Molecular Probes, Eugene, Oreg.). The most preferred fluorophores are the derivatives of fluorescein and particularly 5 and 6-carboxyfluorescein.

Spacer/Linker Moieties

Generally, spacers are used to minimize the adverse effects that bulky labeling reagents might have on hybridization properties of non-nucleic acid probes. Linkers typically induce flexibility and randomness into the probe or otherwise link two or more nucleobase sequences of a probe or component polymer. Preferred spacer/linker moieties for the nucleobase polymers of this invention consist of one or more aminoalkyl carboxylic acids (e.g. aminocaproic acid) the side chain of an amino acid (e.g. the side chain of lysine or ornithine) natural amino acids (e.g. glycine), aminooxyalkylacids (e.g. 8-amino-3,6-dioxaoctanoic add), alkyl diacids (e.g. succinic acid), alkyloxy diacids (e.g. diglycolic acid) or alkyldiamines (e.g. 1,8-diamino-3,6-dioxaoctane). Spacer/linker moieties may also incidentally or intentionally be constructed to improve the water solubility of the probe (For example see: Gildea et al., *Tett. Lett.* 39: 7255–7258 (1998)). Preferably, a spacer/linker moiety comprises one or more linked compounds having the formula: $-Y-(O_m-(CW_2)_n)_o-Z-$. The group Y has the formula: a single bond, $-(CW_2)_p-$, $-C(O)(CW_2)_p-$, $C(S)(CW_2)_p-$ and $-S(O_2)(CW_2)_p$. The group Z has the formula NH, $NR^2$, S or O. Each W is independently H, $R^2$, $-OR^2$, F, Cl, Br or I; wherein, each $R^2$ is independently selected from the group consisting of: $-CX_3$, $-CX_2CX_3$, $-CX_2CX_2CX_3$, $-CX_2CX(CX_3)_2$, and $C(CX_3)_3$. Each X is independently H, F, Cl, Br or I. Each m is independently 0 or 1. Each n, o and p are independently integers from 0 to 10.

Hybridization Conditions/Stringency

Those of ordinary skill in the art of nucleic acid hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probe/target combination is often found by the well known technique of fixing several of the aforementioned stringency factors and then determining the effect of varying a single stringency factor. The same stringency factors can be modulated to thereby control the stringency of hybridization of a PNA to a nucleic acid, except that the hybridization of a PNA is fairly independent of ionic strength. Optimal stringency for an assay may be experimentally determined by examination of each stringency factor until the desired degree of discrimination is achieved.

Suitable Hybridization Conditions

Generally, the more closely related the background causing nucleic acid contaminates are to the target sequence, the more carefully stringency must be controlled. Blocking probes may also be used as a means to improve discrimination beyond the limits possible by mere optimization of stringency factors. Suitable hybridization conditions will thus comprise conditions under which the desired degree of discrimination is achieved such that an assay generates an accurate (within the tolerance desired for the assay) and reproducible result. Aided by no more than routine experimentation and the disclosure provided herein, those of skill in the art will easily be able to determine suitable hybridization conditions for performing assays utilizing the methods and compositions described herein.

Blocking Probes

Blocking probes are PNA, nucleic add or non-nucleic acid probes which can be used to suppress the binding of the probing segment of the probing polymer to a non-target sequence. Preferred blocking probes are PNA probes (See: Coull et al., WIPO publication No. WO98/24933). Typically blocking probes are closely related to the probing segment and preferably they comprise a point mutation of the probing segment. It is believed that blocking probes operate by hybridization to the non-target sequence to thereby form a more thermodynamically stable complex than is formed by hybridization between the probing segment and the non-target sequence. Formation of the more stable and preferred complex blocks formation of the less stable non-preferred complex between the probing segment and the non-target sequence. Thus, blocking probes can be used with the methods and compositions of this invention to suppress the binding of the nucleobase polymer to a non-target sequence.

II. The PD-Loop and Methods of Formation and Use

In one embodiment, this invention relates to compositions prepared by selective hybridization of a nucleobase probe to double stranded nucleic acid, wherein the nucleic acid need not be chemically or thermally denatured. Specifically, the composition comprises a double stranded nucleic acid having at least one homopurine site and one or more PNA oligomers (at times the PNA oligomers will be referred to herein as "openers") which hybridize to the one or more homopurine sites to thereby create an extended open region inside the double stranded nucleic acid. To the extended open region of the double stranded nucleic acid is then hybridized a nucleobase polymer. Preferably, the nucleobase polymer hybridizes to the extended open region to thereby form a double stranded hybrid though the hybrid may be of higher order. The nucleobase sequence of the nucleobase polymer which hybridizes to the extended open region is preferably between five and twenty subunits in length and more preferably between seven to sixteen subunits in length.

The complex formed between the double stranded nucleic acid, the one or more PNA oligomers and the nucleobase probe is referred to herein as a PD-Loop. The position in the double stranded nucleic acid at which the PD-Loop forms is referred to herein as a PD-Loop site or a complex forming site. Though the literature has suggested that the "D" of the "PD-Loop" has been used to signify DNA, no such limitation is intended to apply herein since any nucleobase polymer may hybridize to the extended open region. Thus, all reference herein to a PD-Loop is not intended to limit the possible composition of the nucleobase polymer.

PNA oligomers are chosen to create the extended open region since they are known to strand invade double stranded nucleic acid to thereby form what has been referred to as a P-loop (See: WIPO published patent applications WO92/20702 and WO92/20703). Preferably the one or more PNA oligomers which hybridize to the one or more homopurine sites are bis-PNAs (See WIPO published patent application number WO96/02558). Bis-PNAs are preferred since they are known to form very stable $PNA_2/DNA$ triplexes. Preferably, the bis-PNAs comprise two segments of five or greater PNA subunits in length, but more preferably six to eight PNA subunits in length. Preferred nucleobases used in the bis-PNAs are thymine, cytosine and pseudoisocytosine. Typically the bis-PNAs are designed to be positively charged. This can be easily accomplished by either incorporating terminal lysine amino acids or by incorporating other positively charged PNA Solubility Enhancers during the chemical assembly of the polymer (See: Gildea et al., PNA Solubility Enhancers, Tett. Lett. 39: 7255–7258 (1998)).

Preferably, there are at least two homopurine sites which exist on the same strand. The homopurine sites are preferably separated by between zero to eleven nucleotides or more preferably separated by between three to ten nucleotides. The PNA oligomers which hybridize to the two homopurine sites are preferably bis-PNAs comprising two segments of five to eight PNA subunits in length. This preferred embodiment generates an extended open region of the double stranded nucleic acid to which the nucleobase polymer can hybridize wherein the extended open region is opposite to the homopurine site or sites.

In one embodiment, the nucleobase polymer is a reporter probe labeled with a detectable moiety. Non-limiting examples of detectable moieties include haptens, enzymes, fluorophores, chromophores, chemiluminescent compounds and a radioisotopes. In addition, the reporter probe may be labeled with a ligand which can cut the double stranded nucleic acid. In another embodiment the nucleobase polymer is a capture probe used to immobilize the double stranded nucleic acid. For example, the capture probe could be labeled with biotin so that once the PD-Loop is formed it can be captured using a surface coated with avidin or streptavidin. In still another embodiment, the nucleobase polymer is a primer. Suitable primers include nucleic acid oligomers as well as PNAs modified to comprise a 3'-hydroxyl group See: Lutz et. al., J. Am. Chem. Soc., 119: 3171–3178 (1997)).

In yet another embodiment, the hybrid formed between the nucleobase probe and the exposed strand of the double stranded nucleic acid forms a restriction site which can be cut by a restriction enzyme. Once the cut is made, the PD-Loop can be dissembled by modifying the ionic strength, pH or temperature of the sample. Once the PD-Loop is dissembled, the remaining double stranded nucleic acid will comprise a nick but will not be cut.

In still another embodiment, this invention relates to a method for hybridizing a nucleobase polymer to a double stranded nucleic acid to thereby form a PD-Loop. According to the method, a double stranded nucleic acid comprising at least one homopurine site is chosen. To the one or more homopurine sites are hybridized one or more PNA oligomers to thereby create an extended open region inside the double stranded nucleic acid. To this extended open region is then hybridized a nucleobase polymer. This method for hybridizing a nucleobase polymer to a double stranded nucleic acid is unique and useful since the duplex need not be chemically or thermally denatured.

In a preferred embodiment, the PD-Loop is formed by first treating the double stranded nucleic acid and the one or more PNA oligomers under conditions of low ionic strength. These conditions favor strand invasion by the PNA oligomers. Once formed, the complex having the extended open region, formed by the hybridization of the PNA oligomers to the double stranded nucleic acid add, may then be subjected to conditions of higher ionic strength which may be more suitable for the formation of the hybrid between the nucleobase polymer and the extended open region of the double stranded nucleic acid.

Preferably, there are at least two homopurine sites which exist on the same strand and which are separated by between two to eleven nucleotides or more preferably separated by between three to ten nucleotides. The PNA oligomers which hybridize to the two homopurine sites are preferably bis-PNAs comprising two segments of five to eight PNA subunits in length. This preferred embodiment generates an extended open region of the double stranded nucleic acid into which the nucleobase polymer can hybridize wherein the extended open region is opposite to the homopurine site or sites.

It is far from being obvious that PD-Loops can be assembled. For example, the extended open region formed within the nucleic acid duplex may not create a space which is large enough to allow a hybrid to form between the strand of the nucleic acid and the nucleobase polymer since two bulky $PNA_2/DNA$ triplexes already exist in this location. Indeed, it has been shown that binding of short oligonucleotides to small RNA loops is not always sterically favorable.

The formation of the PD-Loop has several potential applications. In on embodiment, the nucleobase polymer is a capture probe. For example the capture probe is labeled with a ligand such as biotin which interacts with a substrate to thereby facilitate capture of the PD-Loop complex. In a preferred embodiment, a surface is coated with a substrate such as avidin or streptavidin to which the ligand, such as biotin, will bind. Capture of the PD-Loop can be used to extract double stranded nucleic acid from a sample. In one embodiment, such an extraction procedure has been used to enrich a library (See: Example 1). In this model system, the DNA library was enriched by a factor of approximately $10^3$ in only one cycle of enrichment.

In another embodiment, the nucleobase polymer is a reporter probe labeled with a detectable moiety. Labeled reporter probes can be used in in-vitro, in-vivo and in-situ applications to thereby allow one to detect, identify or quantitate the presence of the double stranded nucleic acid in a sample of interest. The method may find applications in genomics and DNA nanotechnology.

Since the PD-Loop structure is a new way to hybridize oligonucleotides with double stranded nucleic acid, this structure may find applications for diagnostics, isolation and selection of specific sequences on double stranded nucleic acid and for the selective manipulation of nucleic acid duplexes. Additionally, there are several advantages associated with the PD-Loops of this invention. For example, the hybridization of the nucleobase polymer exhibits remarkable selectivity. Moreover, the methods and compositions can be used to isolate imprinted genes carrying post synthetic modifications. Alternatively, the PD-Loop can be used to selectively isolate a double stranded nucleic acid fragment from a very complex mixture of nucleic acid. When the nucleic acid must be preserved in the intact, biologically active form, this approach has significant advantages over the PCR amplification because the formation of the PD-Loop does not require chemical or thermal denaturating of the double stranded nucleic acid.

III. Sanger Sequencing And Amplification

In one preferred embodiment, the PD-Loop can be used to generate sequence analysis or amplification of the double stranded nucleic acid. In this embodiment, the nucleobase polymer is a primer. Suitable primers include nucleic acids, nucleic acid analogues, nucleic acid mimics and other polymers which comprise a 3'-hydroxyl group and which can be extended by a polymerase when hybridized to an nucleic acid template. For example, the nucleobase probe could be a modified PNA comprising a 3'-hydroxyl group (See: Lutz et. al., *J. Am. Chem. Soc.,* 119: 3171–3178 (1997)).

According the amplification method, the PD-Loop is formed as previously described and then polymerase dependent primer extension is initiated under suitable polymerase extension conditions. Under isothermal conditions, this process generates a detectable single stranded copy of the template strand. The single stranded copy will be detectable by numerous well known methods but preferably the copy is labeled with one or more detectable moieties. For example, the generated copy can be directly labeled either by incorporation of labeled nucleotide triphosphates or by the use of a labeled nucleobase polymer primer.

According to the sequencing method, the PD-Loop is formed as previously described and then polymerase dependent primer extension is initiated under suitable Sanger sequencing conditions. Under isothermal conditions, this process generates Sanger sequencing ladders from the double stranded nucleic add template. The Sanger sequencing ladders can then be analyzed by conventional techniques to thereby determine the sequence of the double stranded nucleic acid. Though any polymerase which can operate with a double stranded template will be suitable, exemplary polymerases include Klenow DNA polymerase, T7 DNA polymerase, Sequenase, DNA polymerase 1 and phi29 polymerase.

Generally, the analysis of the Sanger sequence ladders will comprise an electrophoretic separation. Preferably, the primer will be labeled so that the ladder can be directly analyzed once it has been generated. Alternatively, the nucleotide triphosphates are labeled and incorporated into the Sanger sequence ladders during polymerase extension. Preferred labels include fluorophores and radioisotopes. Most preferably, the labels are independently detectable fluorophores such that each sequence ladder (terminated in one of the four dideoxynucleotide triphosphates) can be independently detected. The facilitates efficient multiplex analysis of the Sanger sequence ladder using commercially available automated instrumentation. Because the template comprised complementary double stranded nucleic acid, determination of the sequence of one strand will usually be sufficient to determine the sequence of the other strand.

Once the first set of sequence data has been obtained, it can be analyzed for sequences suitable for the generation of new PD-Loops within the double stranded nucleic acid. Preferred complex forming sites comprise two homopurine sequences on the same strand separated by between two to eleven nucleotides. Once identified, new PD-Loops can be formed using one or more PNA oligomers and a primer which will be polymerase extended either upstream or downstream from the original PD-Loop forming site. Consequently, it is possible to read the double stranded nucleic acid in both directions using properly designed PNA "openers" and nucleobase polymer primers.

According to the method, a new site for a PD-Loop is chosen. Next, the one or more PNA oligomers is hybridized to the one or more homopurine sites to thereby create an extended open region inside the double stranded nucleic acid. To the extended open region of the double stranded nucleic acid template is hybridized a primer which can be extended by a polymerase. Depending on the nature of the PD-Loop chosen, extension of the primer will occur either upstream or downstream to the prior sequence read. Once the PD-Loop is fully formed, the primer is extended with a polymerase, under suitable Sanger sequencing conditions, to thereby form Sanger sequencing ladders from the double stranded nucleic acid template. The Sanger sequencing ladders are then analyzed using conventional techniques to thereby determine the sequence of the double stranded nucleic acid. This method can then be repeated until no more suitable homopurine sites are found which would allow one to form a PD-Loop, until the entire sequence of the double stranded template is determined or until the desired sequence information is obtained.

In still another embodiment, this invention pertains to a Sanger sequence ladder which is generated isothermally from a double stranded nucleic acid template without the application of chemical or thermal denaturing conditions.

Because this sequencing method requires invasion of the double stranded nucleic acid, it is quite selective. Thus, the method can be operated in the presence of large excesses of unrelated double stranded nucleic acid since mispriming will typically not occur. Because the nucleobase polymer, which acts as a primer, can be quite short (approximately 13–15 subunits in length), excellent target specificity, including point mutation discrimination, can be achieved. Moreover, the sequencing reaction occurs under isothermal conditions and therefore does not require sophisticated instrumentation such as a thermocyder. It is an additional advantage of the present invention that the nucleic acid which is to be sequenced need not be tediously reduced to a single stranded template. Consequently, this method of sequencing possesses the substantial advantage that little or no sample preparation is required.

IV. Double Stranded Nucleic Acid With A Linked Single Stranded Circularized Nucleic Acid In still another embodiment, this invention is related to a double stranded nucleic acid having a linked single stranded closed circular nucleic acid wherein the single stranded nucleic acid is threaded through the strands of the duplex. This construct will at times be referred to herein as the "Earring". The double stranded nucleic acid can be linear or closed circular. Because the complex can be formed under isothermal conditions, the single stranded closed circular nucleic acid can be topologically linked in close proximity to the site where it was formed provided that the complex is not subjected to denaturing conditions. Because the closed circular single stranded nucleic acid is topologically fixed in the double stranded nucleic acid, the construct may provide a means for the highly localized detection of various marker sequences within genomes.

In preferred embodiments, the single stranded closed circular nucleic acid is labeled with one or more detectable moieties. Non-limiting examples of suitable detectable moieties have been previously described herein. In preferred embodiments, the presence or quantity of the label of the single stranded dosed circular nucleic add can be determined by detecting or quantitating the detectable moiety. Consequently, the presence or quantity of the double stranded nucleic add can likewise be detected or quantitated by correlation with the presence or quantity of the detectable moiety since the presence of the single stranded closed circular nucleic acid will be proportional to the presence or quantity of the double stranded nucleic acid.

In another preferred embodiment, the single stranded closed circular nucleic acid is labeled with a ligand of a ligand/substrate affinity pair. Thus, a substrate coated surface can be used to immobilize the double stranded nucleic acid. For example, the single stranded closed circular nucleic add could be labeled with biotin so that the complex comprising the double stranded nucleic add can be captured using a surface coated with avidin or streptavidin. Many other affinity pairs suitable for capturing the complex are well known in the art.

The invention further relates to a method of forming a double stranded nucleic acid having a linked single stranded closed circular nucleic acid wherein the single stranded nucleic acid is threaded through the strands of the duplex. According to the method, the double stranded nucleic acid is invaded to thereby create an extended open region inside the double stranded nucleic acid. Methods for invading double stranded nucleic acid are known in the art and preferred methods for creating an extended open region have been previously described herein. To the extended open region is then hybridized an oligonucleotide in such a way that the two termini of the oligonucleotide are complementary to the exposed double stranded nucleic acid and are juxtapositioned to one strand of the double stranded nucleic acid. Once this PD-Loop is formed, the two termini of the oligonucleotide are then ligated to thereby form the single stranded closed circular nucleic acid. Preferably, the termini are ligated using a ligase but optionally the termini can be ligated using chemical methodology.

It is an advantage of the present invention that point mutation discrimination can be achieved in the ligation of the hybridized single stranded nucleic acid. More specifically, the PD-Loop can be designed such that a single mutation occurring between the nucleobase probe to be ligated and the exposed strand of the double stranded nucleic acid will cause the ligation to fail. Consequently, this method can be used to identify, under isothermal conditions, a point mutation of a double stranded nucleic acid.

In yet another embodiment, the single stranded closed circular nucleic acid is used in a signal amplification methodology. According to the method, a primer is hybridized to the single stranded closed circular nucleic acid. A polymerase dependent primer extension reaction is then initiated to thereby generate one or more copies of the single stranded closed circular nucleic add. Suitable polymerases have been previously described herein. Preferably, numerous copies of the single stranded closed circular nucleic acid will be produced such that it results in efficient signal amplification. In the most preferred embodiment, a hybridization site for a reporter probe is repeated numerous times per single stranded copy of the closed circular nucleic acid.

In one preferred embodiment, the one or more single stranded copies of the circularized nucleic add are detected using a labeled nucleobase probe. The labeled nucleobase probe can be a reporter probe labeled with suitable detectable moieties as previously described herein. Alternatively, the labeled nucleobase probe is a dark probe as previously defined herein. In one embodiment, signal amplification is detected by hybridizing the nucleobase probe (reporter probe or dark probe) to the single stranded copy or copies wherein the hybrid is detected using conventional methodologies. Here the dark probes are preferred since excess probe does not necessarily need to be removed.

In other embodiments, the labeled probe can be indirectly linked to one or more segments of the single stranded copy. For example, the labeled probe can be indirectly sequence specifically linked to one or more segments of the copy or copies of the dosed circular nucleic acid as for example using an all probe triplex (See: European Patent Application No. EP 849,363). This linkage is indirect since the labeled probe of the probe triplex need not directly interact with the hybridization site.

Having described the preferred embodiments of the invention, it will now become apparent to one of skill in the art that other embodiments incorporating the concepts described herein may be used. It is felt, therefore, that these embodiments should not be limited to disclosed embodiments but rather should be limited only by the spirit and scope of the following claims.

EXAMPLES

Example 1: PD-Loop Formation

PNA Openers

PNA oligomerization and purification was performed using methods known in the art. The following bis-PNA openers were used in this study (their identity was confirmed by MALDI-TOF mass spectrometry):

PNA1:  H(Lys)$_2$-TTTJTTJJ-(egl)$_3$-CCTTCTTT-LysNH$_2$  (+4)

PNA2:  H(Lys)$_2$-JTTJJJJT-(egl)$_3$-TCCCCTTC-LysNH$_2$  (+4)

PNA3:  H(Lys)$_3$-TTJJTTT-(egl)$_3$-TTTCCTT-LysNH$_2$  (+5)

As with peptides, PNA sequences are written from amino terminus to carboxy terminus and T, C, and J denote here the N-1 alkylated pyrimidine nucleobases connected with N-(2-aminoethyl)glycine backbone via methylenecarbonyl linkers, respectively. H means a free amino group. NH$_2$ means a terminal carboxyamide. Lys denotes a lysine residue. Egl denotes the 8-amino-3,6-dioxaoctanoic add groups, which serve as linkers connecting two PNA oligomers in bis-PNA. The J base denotes pseudoisocytosine. All bis-PNAs carry multiple positively charged lysine residues at their J-containing halves because such polycationic PNA constructions are characterized by high complex stability and high binding specificity. Numbers in parentheses indicate the total charge of PNA oligomers.

DNA Oligomers

All nonphosphorylated ODNs (adapters, primers, tags, etc.) were obtained from Operon Technologies (Alameda, Calif.). The biotinylated ODN tags used in this study were as follow:

```
ODN 1:   5'GAAGGTTCGAAGG3'-biotin      Seq. ID 1

ODN 2:   5'AAGGTTCGAAG3'-biotin;       Seq. ID 2

ODN 3:   biotin-5'GAAGGCTGGAAGGA3'     Seq. ID 3
```

Biotin was conjugated with ODNs through a flexible linker. Both 3'- and 5'-ends of ODNs were chosen for conjugation just to check the possible steric interference of PD-Loop structure with streptavidin binding. The results (vide infra) demonstrate that either end of the ODN is accessible for protein binding. The ODNs 1 and 2 were used as tags for capturing the plasmnids while ODN 3 was used for isolation of a yeast dsDNA fragment.

Plasmids

Plasmids carrying the appropriate inserts were obtained by cloning of the corresponding ODNs into the BamH I site of the pUC19 vector, with subsequent sequencing. In all cases the inserts were verified by direct sequencing. Plasmid inserts were as follows:

```
(pPL3 plasmid, n=3)

-5'TCCCCTTCGAACCTTCTTT3'-    Seq. ID 4

-3'AGGGGAAGCTTGGAAGAAA5'-    Seq. ID 5

(pPL11 plasmid, n=11)

-5'TCCCCTTCCTTCGAACCTTCCTTCTTT3'-     Seq. ID 6

-3'AGGGGAAGGAAGCTTGGAAGGAAGAAA5'-     Seq. ID 7
``` where n indicates the number of nucleotides separating adjacent bis-PNA binding sites (for PNAs 1 and 2). These PNA binding sites are in bold underlined text.

Yeast DNA

Genomic DNA from S. cerevisiae strain AB1380 (GenomeSystems, St. Louis, Mo.) was isolated in agarose inserts and was stored at low temperatures. Yeast DNA was retrieved from the inserts with β-Agarose I (New England Biolabs, Inc., Beverly, Mass.) into appropriate buffer isolution, then digested with the Mse I restriction enzyme and ligated with 50 pmols of Mse I-adapter.

```
     5'-TCTCCAGCCTCTCACCGCAT-3'       Seq. ID 8

3'-AGTGGCGTAAT-5'            Seq. ID 9
```

The fill-in reaction was performed at room temperature with the Klenow polymerase to generate blunt ends. The yeast target site we chose was of the n=4 type:

```
       -5'TTTCCTTCCAGCCTTCTTT3'-      Seq. ID 10

-3'AAAGGAAGGTCGGAAGAAA5'-     Seq. ID 11
```

GenBank accession number Z38060; co-ordinates 15546–15564; the bis-PNA binding sites (for PNAs 1 and 3) are in bold underlined text.

Plasmid Capture Protocol

We used full-length control (pBR322) and target (pPL3 or pPL11) plasmids linearized with the Aat II restriction enzyme. Binding of a pair of PNA openers (PNAs 1 and 2) to plasmids was carried out in 25 mM MES buffer (pH 6.1) at 37° C. for 2–20 h with the PNA concentration about 0.5 $\mu$M. To avoid binding of PNA openers with the partially complementary biotinylated ODN, free openers were removed from the samples by gel filtration. After subsequent binding of biotinylated ODNs (mostly, ODN 1) at 37° C., the free ODN was removed from samples by gel filtration. Magnetic separation was performed in accordance with the Dynal protocol using BioMag Streptavidin magnetic beads (PerSeptive Diagnostics, MA). The beads collected with a magnet were then washed extensively several times and captured DNA was released from the magnetic beads by incubation at 65° C. for 20 min in TE buffer (pH 7.5) with 1 M NaCl under gentle shaking. DNA eluted from the beads was ethanol precipitated, resuspended and typically analyzed by electrophoresis in 1% agarose gel with subsequent ethidium bromide staining and the CCD camera detection. The quantitative analysis was done by processing the images with the IC-1000 Digital Imaging System (Innotech Scientific Corp., CA).

Transformation Analysis

We also used a more sensitive method to quantify the results of affinity capture experiments. In this method, an enriched mixture of control (pBR322) and target (pPL3) linear plasmids eluted from magnetic beads were converted into circular form by T4 DNA ligase (Gibco BRL/Life Technologies, MD). Re-circularized plasmids were then used for transformation of competent E. coli cells. Transformed bacterial cells were spread onto XGal-containing agar plates and were grown up overnight at 37° C. Transformants carrying the pBR322 plasmid form white colonies on these selective media while transformants carrying the pPL3 plasmid form blue colonies on the same plates and thus can be easily distinguished.

Yeast DNA Capture Protocol

To isolate a specific yeast dsDNA fragment, we followed mainly the basic plasmid capture protocol with minor modifications. The only significant change was that to release the captured dsDNA from magnetic beads we now incubated samples at lower temperature and under lower salt concentration: at 47° C. for 20 min in TE buffer (pH 7.5) with 50 mM NaCl. This modification of the capture protocol allows retention of the PNA openers on DNA during all rounds of subsequent enrichment, thus avoiding the time-consuming step of re-targeting of DNA samples with the openers in the next round of separation. Therefore, PNA openers (PNAs 1 and 3) were targeted to 250 ng of yeast DNA ($1.5 \cdot 10^7$ copies of the yeast genome) only at the beginning of the first round. During each round of separation, the captured samples were extensively washed out, released from the beads, rebound with ODN 3 and another round was initiated. After each round, an aliquot of captured DNA was collected and amplified using AmpliTaq DNA polymerase (Perkin-Elmer Cetus, CT) by 35 cycles of non-specific PCR using an adapter-specific primer,

```
        5'TCTCCAGCCTCTCACCGCAT3'       Seq. ID 12
``` and was analyzed by electrophoresis in 1.5% agarose gel.

Analysis of Captured Yeast DNA

To analyze the captured yeast DNA fragment, we re-amplified the DNA material from the bands corresponding to this fragment in the agarose gel obtained after 3rd and 5th rounds of enrichment. The PCR amplification in both cases resulted in a homogeneous DNA fragment of the expected size. The amplified material obtained after the 3rd round was digested by several restriction enzymes (Alu I, Mbo I, Dde I and Rsa I). In all cases, the obtained restriction maps coincided with expected ones confirming the purity and identity of the captured fragment. Sequence of the material amplified after 3rd and 5th rounds of enrichment was confirmed by cycle sequencing (Commonwealth Biotechnologies, Inc., VA).

Detection of PP-Loop Formation By Gel Electrophoresis

PP-Loop (PP-Loop designated here because the nucleobase polymer is a PNA) formation was accomplished using two PNA openers (PNA 1 and PNA 2) and a third biotinylated PNA probe (See FIG. 1):

```
PNA 4: biotin-(Lys)2-GAAGGTTCGAAGG-(Lys)2NH2
```

The three PNA and streptavidin were combined sequentially with a 350 bp fragment of pPL3 containing an inserted target site for the openers (see Plasmids above). Portions were retained following each addition for analysis by the gel-shift. Firstly, the binding of 0.1 $\mu$M PNA openers was carried out in 25 mM MES buffer (pH 6.1) at 37° C. for 2.5 h. Non-bound openers were removed by gel filtration through MicroSpin G-50 columns (Pharmacia Biotech) and then PNA 4 was added at 0.1 $\mu$M. Streptavidin was then added to a portion of this sample to selectively yield an extra retardation. Electrophoresis of the retained samples was done in 0.5×TBE buffer (pH 8.0) in 7.5% polyacrylamide gels. DNA bands were visualized by staining with ethidium bromide and detected by CCD camera.

Figure 2:
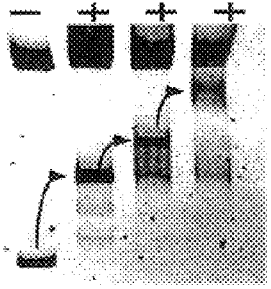
FIG. 2 is an image of a gel containing experimental data.

FIG. 2 shows that as each component is added to the reaction the mobility of the pPL3 fragment is reduced. This data is consistent with the formation of a PP-Loop.

Detection of PD-Loop Formation By Plasmid Capture

Figure 3:
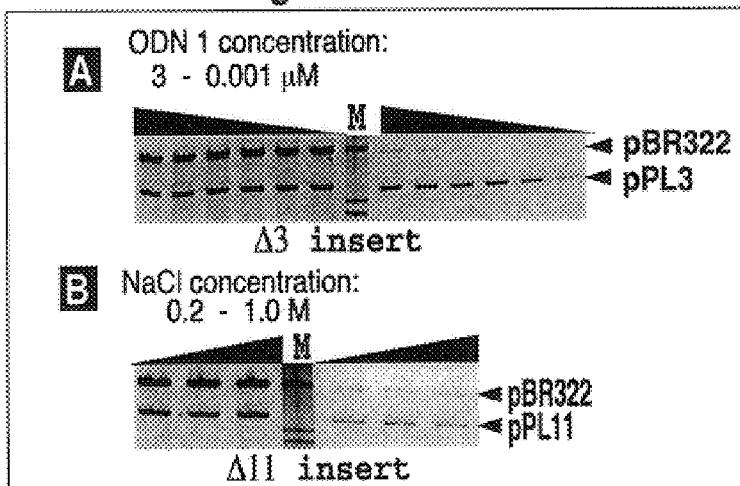
FIG. 3 is an image of a gel containing experimental data.

An affinity capture method was also used for detection of stable PD-Loop where the reporter group on the oligonucleotide probe was a biotin residue that could be used for selective capture, by magnetic beads covered by streptavidin, of full-length linear plasrnid DNAs with corresponding inserts. The inserts used consisted of mixed purine-pyrimidine sequences of various lengths flanked by two short binding sites for PNA openers (see Seq. ID Nos. 4/5 and 6/7). FIG. 3 shows the results of the affinity capture procedure. These results are consistent with PD-Loop formation. Control experiments showed that in the absence of any component necessary for PD-Loop formation (i.e., PNA openers, biotinylated ODN or target site), the capturing effect disappeared (data not shown). The effect was also absent when used ODN 2 was used instead of ODN 1. ODN 2 differs from ODN 1 by the absence of two terminal nucleotides.

The following are the conclusions from our capture experiments: 1) the observed capture is due to the PD-Loop formation; 2) PD-Loops remain stable at high salt concentration (at least 1 M NaCl); 3) PD-Loops are formed with openers when the opener binding sites are separated by as many as 11 bp (the pPL11 plasmid), and; 4) stability of the PD-Loop structure and the efficiency of its formation decrease with increasing distance between the opener binding sites.

The data in FIG. 3 also demonstrates that at high concentrations of ODN significant non-specific capture is observed. This nonspecific capture is due to the detection method rather than non-specific formation of PD-Loops. In fact, no capturing at all was observed in case of the control plasmid alone even in the presence of all components needed for the formation of the PD-Loop complex. Further data (not included) indicate that non-specific capture at high ODN concentration is random co-capture of control DNA due to aggregation with target DNA molecules carrying the PD-Loop. Conversely, FIG. 3 shows that very little non-specific capture occurs at lower concentrations of ODN.

High Specificity of PD-Loop Formation

To support our anticipation that the PD-Loop formation must be an exceptionally sequence-specific process, we isolated a specific fragment of duplex DNA from a digest of the entire yeast genome. Among many suitable sites for the PD-Loop formation in the yeast genome, unique 19-bp-long site on S. cerevisiae chromosome IX consisting of two binding sites for PNA openers 1 and 3 separated by a 4-bp-long mixed purine-pyrimidine sequence was chosen (see Yeast DNA capture protocol, above). Biotinylated ODN 3 was used as a probe. Digestion of the yeast genome with the Mse I restriction enzyme yielded a 863-bp-ong desired DNA fragment, which is about 1/17,000 part of the S. cerevisiae genome.

Five rounds of the magnetic separation procedure were performed. Aliquots of captured DNA collected after each round of enrichment were analyzed by non-specific PCR amplification using a primer complementary to a special adapter ligated to both ends of all fragments of the original digest (see Analysis of captured yeast DNA, above). This assay amplified all DNA fragments captured on magnetic beads after the PD-Loop formation. If the desired fragment of yeast DNA were captured by our technique, it would be detected as a fragment with the size of 903 bp (the fragment plus two adapters). Note that we used PCR only as a detection method at the end of one, two, three, four and five rounds of enrichment. No intervening amplification of captured material was performed between rounds.

Figure 4:
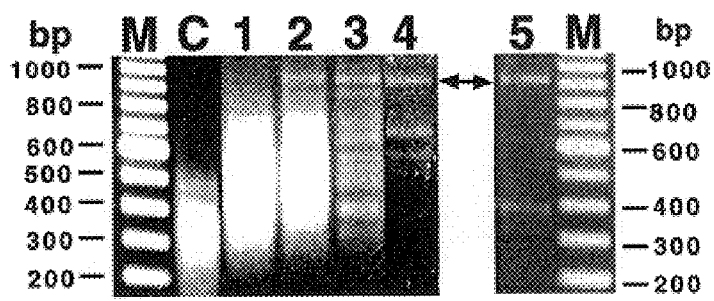
FIG. 4 is an image of a gel containing experimental data.

FIG. 4 shows results that demonstrate sequence specificity of the PD-Loop structure. After three rounds of the PD-Loop formation/separation the variety of captured fragments dramatically reduced and the desired 903-bp-long DNA fragment could be selectively isolated. Additional rounds of enrichment, the 4th round and especially the 5th round, further reduced the amount and variety of captured fragments leaving very few non-specific fragments. A band corresponding to our 903-bp fragment was the only major band that systematically appeared in the subsequent rounds of the capture procedure. Restriction analysis and sequencing performed after the 3rd and the 5th rounds confirmed that the DNA fragment marked by arrows in FIG. 4 was the expected fragment.

Demonstration of PD-Loop Specificity By Transformation of E. coli

The high specificity of the PD-Loop formation is at the limit of the photometric detection of the CCD camera when the magnetic separation is followed by the gel-electrophoresis assay. For more accurate estimations of specificity of the PD-Loop formation a different approach was used. First, the PD-Loop affinity capture procedure was applied to a mixture of control and target plasmids. Then, competent E. coli cells were transformed by re-circularized plasmid DNA eluted from the magnetic beads. Bacterial transformants were then grown on selective media. Transformants carrying pBR322 (control) and pPL3 (target) plasmids formed colonies of different color on the XGal-containing agar plates. Hence, the enrichment of the initial plasmid mixture in pPL3 plasmids by the procedure (and therefore the specificity of the PD-Loop formation) was directly quantified by counting the number of colonies of each type. The results were compared to results obtained by transformation with plasmid mixture that had not been affinity enriched. The enrichment transformation experiments indicated that the relative specificity of PD-Loop formation for the target and non-target plasmids was approximately 1,000 (See Table 1).

TABLE 1

Enrichment[a] of the pPL3 target plasmid (blue clones) from a mixture with control plasmid pBR322 (white clones) measured by affinity capture via PD-loops combined with the microbiological analysis

| No white/blue colonies | Enrichment | Comments |
|---|---|---|
| Experiments: | | |
| 1  120/8600 | 460 | all components present [b] |
| 2  0/171 | >1100 | all components present [c] |
| 3  3/900 | 1900 | all components present [d] |
| 4  240/23500 | 630 | all components present [e] |
| Controls: | | |
| 5  0/0 | ND | no ODN tag [e] |
| 6  0/0 | ND | no PNA openers [e] |
| 7  1/0 | ND | no target plasmid (pPL3) [e] |

[a] Enrichment is given relative to the initial control/target plasmid ratio (6.4:1 as measured by the microbiological assay) and is determined in transformation experiments after capture using PNA 1 and 2 as openers and ODN 1 as a probe (0.8 pmols).
[b,c,d] After binding with PNA openers and removal the free PNA the plasmid samples in this series of transformation experiments (No 1–3) were washed out of non-specifically bound PNA at 37° C. for 1 h in 200, 500 and 1000 mM of NaCl, respectively.
[e] One more series of transformation experiments (No 4–7) was done with above mentioned washing procedure repeated twice: first in 200 mM of NaCl, then in 480 mM of NaCl; both times at 37° C. for 1 h.

Example 2: Isothermal Primer Extension Of The PD-Loop

Primer Extension Via PD-Loop

Figure 5:
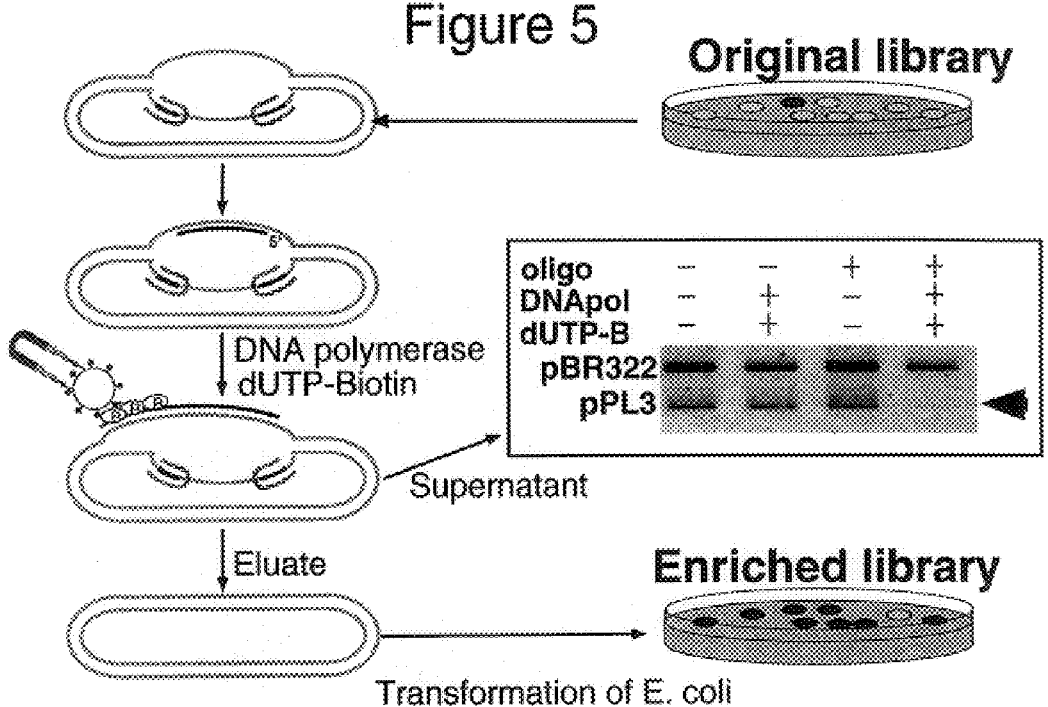
FIG. 5 is an illustration of library enrichment and an image of a gel containing experimental data.
Figure 6:
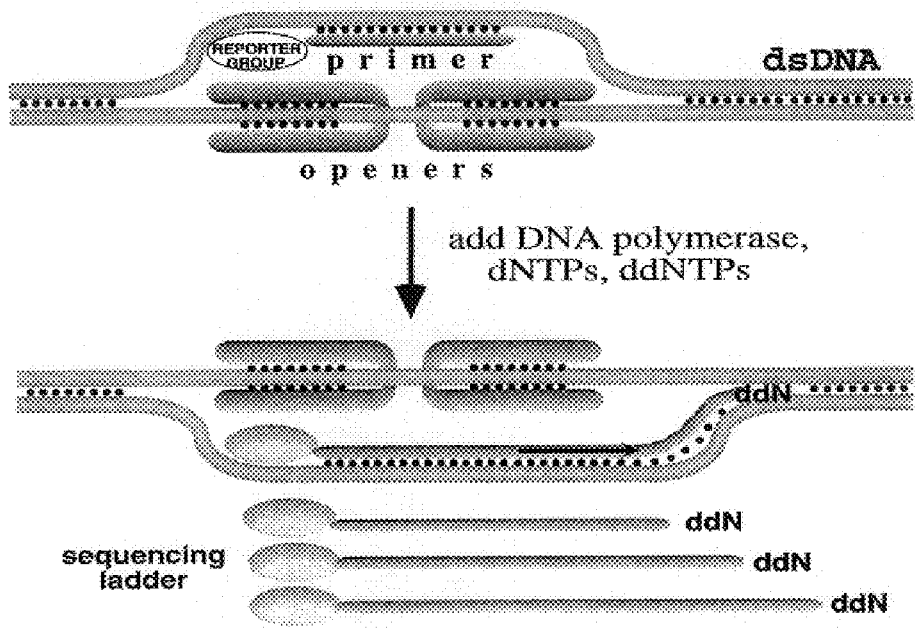
FIG. 6 is an illustration of the process of generating a Sanger sequencing ladder from a PD-Loop.

FIG. 5 shows the design experiment, which demonstrates the ability of the PD-loop to initiate the primer-extension reaction. We used PNAs 1 and 2, and plasmid pPL3 (see Example 1) and the affinity capture on streptavidin coated magnetic beads (see Plasmid Capture Protocol) with microbiological detection (see Transformation Analysis). Biotinylated dUTP served as an indicator of the primer-extension reaction of non-biotinylated ODN by exo⁻Klenow DNA polymerase, which added numerous biotinylated nucleotides to the growing chain. The initial DNA mixture consisted mostly of control pBR322 plasmid and contained only a very small fraction (at approximately 6:1 ratio of control to target plasmids, both in the supercoiled form) of the target pPL3 plasmid. This resulted originally in few colored colonies of E. coli transformants, bearing the target plasmid and growing on selective agar plates with X-Gal. After PD-loop hybridization of a nonbiotinylated primer, 5'-GAAGGTTCGAAGG-3'Seq. ID No. 18 , the primer extension reaction was carried out in a solution containing 10 mM Tris-HCI, pH 7.5,5 mM MgCl$_2$, 7.5 mM dithiothreitol, 100 μM of each dATP, dGTP and dCTP, 65 μm dTTP and 35 μM biotin-dUTP (Boehringer Mannheim) in a final volume of 30 μl. The reaction was initiated by the addition of 5 units of Klenow polymerase (NEB). After incubation at 37° C. for 1 h, the reaction was stopped by addition EDTA (final concentration 50 mM). The mixture was equilibrated with x1TAE with 0.5 M NaCl, DNA was captured with streptavidin-covered magnetic beads, eluted and after purification by ethanol precipitation transformed into competent cells of E. coli. The several hundred-fold enrichment of original mixture by specific DNA was observed. Also, the discriminative depletion of pPL3 plasmids by magnetic separation after their selective labeling with biotin due to primer-extension reaction was detected by agarose gel electrophoresis. This proved that initially non-biotinylated ODN, which hybridized with dsDNA via the PD-loop formation, was biotinylated due to incorporation of biotinylated dUTP by DNA polymerase in the primer-extension reaction. Multiple biotinylation of the hybridization site thus obtained will be a very convenient for signal amplification. FIG. 5. The primer-extension reaction via PD-loop hybridization as monitored by affinity capture followed by microbiological detection. The white colonies correspond to pBR322 plasmids (control), while the blue colonies (shown as black plaques) correspond to pPL3 plasmids (target). The insert shows the discriminative depletion of pPL3 plasmids by magnetic separation after their selective labeling with biotin due to primer-extension reaction as detected by agarose gel electrophoresis.

Sequencing of Plasmid pPL3

A PD-Loop was formed by combining 0.5 μg of linear plasmid pPL3 (cut with Aat II restriction enzyme) with PNA openers;

PNA 1: H(Lys)$_2$-TTTJTTJJ-(egl)$_3$-CCTTCTTT-LysNH$_2$
PNA 5: H-TCCCCTCC-egl-(Lys)$_2$-egl-JTTJJJJT-LysNH$_2$ where egl, Lys and J denote linker unit, lysine residue and pseudoisocytosine, respectively. A sequencing reaction was performed using the reagents from an AutoRead Sanger sequencing kit (PharmaciaBiotech) and 5 pmoles of 5'-flouresceinated 15-mer oligonucleotide;

5'-Fluor-AAGAAGGTTCGAAGG-3'     Seq. ID 13 as the primer. The reaction was catalyzed by T7 polymerase at 37 ° C. in the presence of 1 μg/μL of single strand binding protein (SSB). An illustration of this process is presented in FIG. 7. As a positive control, the reaction was repeated except that PNA openers were omitted and the plasmid DNA was denatured prior to sequencing with a standard alkali pretreatment. As a negative control, PNA openers were omitted and denaturation with alkali was not performed. Reaction products were separated and analyzed using an ALF sequencer (Pharmacia Biotech).

Figure 7A:
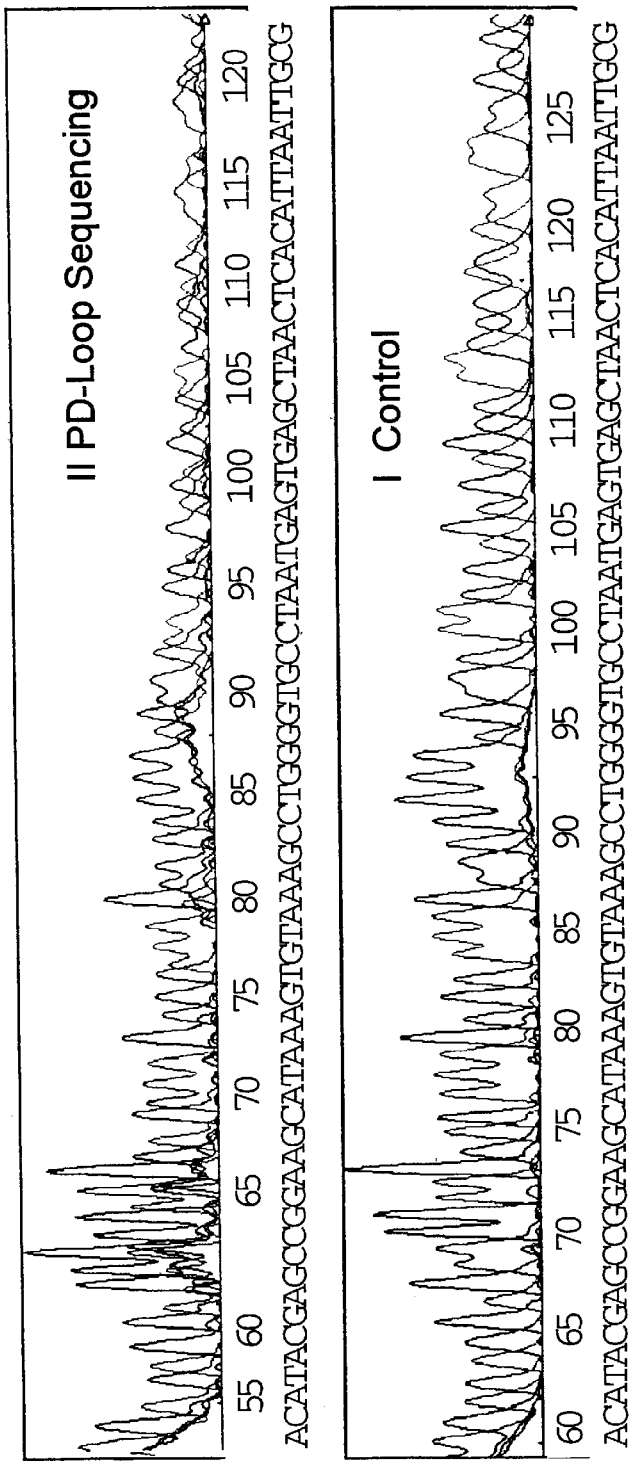
FIG. 7 is a sequence data generated using an automated sequence analyzer.

FIG. 7a shows the results of the positive control reaction (I control) and the PD-Loop reaction (II PD-Loop sequencing). No extension was observed in the case of the negative control reaction (not shown) demonstrating that addition of PNA openers was responsible for the extension seen in the PD-Loop reaction.

Sequencing of pHIV Plasmid in the Presence in Lambda Phage DNA

A PD-Loop sequencing experiment was conducted by combining 0.5 μg of a plasmid, pHIV, containing the following target sequence insert;

pHIV 5'-AGAGGAAGCTACTGGAGGAGA-3'     Seq. ID 14 derived from HIV1 viral strain 92ug037, subtype A with 0.5 μg of phage lambda DNA. The PNA openers used were designed to bind to the pHIV insert;

PNA 6: H(Lys)$_2$TJTJJTTJ-(egl)$_3$-CTTCCTCT-LysNH$_2$    (+4)

-continued

PNA 7: H(Lys)$_2$TCTCCTCC-(egl)$_3$-JJTJJTJT-LysNH$_2$ (+4)

The reaction was primed with 5 pmoles of 5'Flouresceinated oligonucleotide;

5'-Fluor-GAAGCTACTGGAG-3'    Seq. ID 15 and was conducted at 37° C. using the reagents from the AutoRead kit. Reaction products were analyzed as described previously.

Figure 7B:
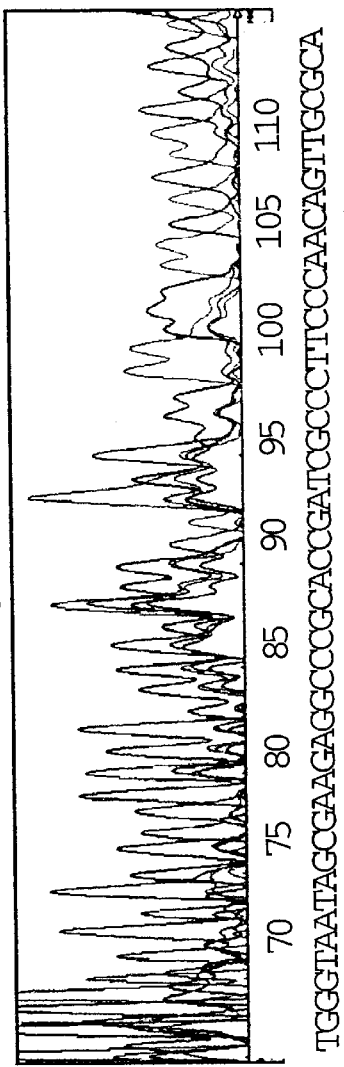

A portion of the sequencing results of the pHIV experiment are shown in FIG. 7b. The results demonstrated that more than 200 nucleobases of pHIV plasmid sequence could be determined in the presence of equal amount of "contaminating" phage DNA.

Example 3: Formation of the Earring

Schematic illustration of the assembly of linked pseudorotaxane III is shown in FIG. 8. Plasmid pPL3 (Example 1) was first digested with PvuII endonuclease resulting in two fragments of 2367 bp and 340 bp length, the latter being target fragment I. The digested DNA was then dephosphorylated by alkaline phosphatase (CIP, New England BioLabs) and combined with PNA openers 1 and 5 (Example 2). In a typical experiment, PNA-DNA complex II was obtained by addition of 10 μL of 0.1 M sodium-phosphate buffer (pH 6.8), 63 μL H$_2$O, and 10 μL each of 20 μM PNA solutions to 7 μL of digested, dephosphorylated plasmid DNA (7 μg or 0.57 pmol), and incubation for 4 h at 37° C. Nonbound PNA openers were then removed by gel filtration (Sephadex G-50, Sigma). To form III, a 10 μL aliquot of sample containing II (~0.7 μg total DNA), 2 μL of 10× ligation buffer (Fermentas), 5 μL H$_2$O, 2 μL of 4 uM ODN 4, and 1 μL T4 DNA ligase (Fermentas, 30 units/μL) were added, and sequentially incubated for 2 h at 16° C., 15 min at 45° C., and 2 h at 16° C.

The oligonucleotide (ODN 4) of appropriate sequence for ligation and labeled with a biotinylated reporter (Ibioteg$^{TM}$) was obtained from Operon. ODN 4 was obtained from Operon. Before electrophoresis, samples were desalted by gel filtration, phenol/chloroform extracted, ethanol precipitated, and redissolved in 10 μL TE (10 mM Tris, 0.1 mM EDTA, pH 7.4). Complex III* was obtained from III by incubation of 10 μL of III with 2 μL of 1 mM streptavidin for 1 h at 37° C. The electrophoretic analysis was performed in non-denaturing 10% polyacrylamide gels using TBE buffer (90 mM Tris-base, 90 mM boric acid, 2 mM EDTA, pH 8.0). Electrophoresis was run at 250 V, 20 mA for 4 h at room temperature. The gels were stained with ethidium bromide and scanned with a CCD camera using the IS-1000 digital imaging system (Alpha Innotech Corporation).

Figure 9A:
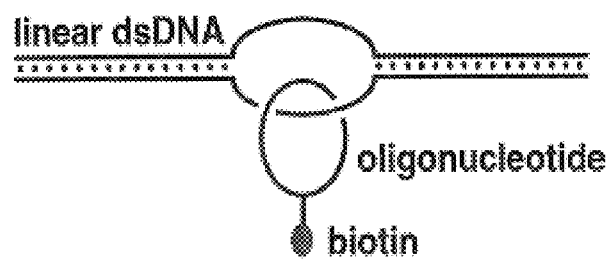
FIG. 9*a* is an illustration of an "Earring".
Figure 9B:
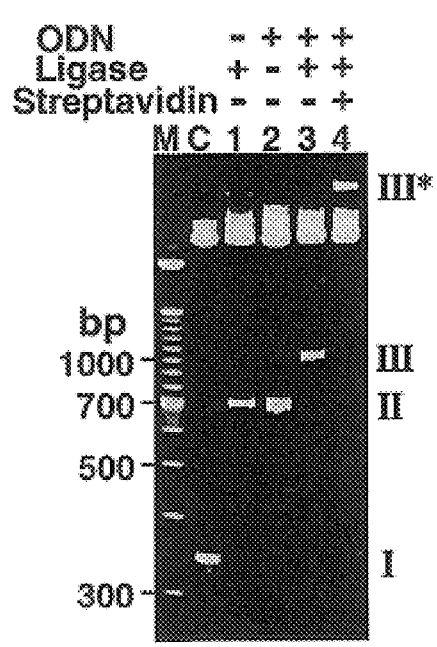
FIG. 9*b* is an image of a gel containing experimental data.

FIG. 9b shows the effect of adding the various components to the reactions. Lane M is a size marker ladder. Lane C is a control lane showing the position of II, the DNA fragment with bound PNA openers. Lanes 1 and 2 are controls showing the effect of combing II with either ligase or ODN 4, respectively. Lane 3 shows the effect of combining II with both ligase and ODN 4. Lane 5 shows the effect of combining II with both ligase and ODN 4, followed by incubation with streptavidin. From the results it is clear that only the addition of ligase and ODN 4 result in formation of stable complex III and that complex III must contain ODN 4 since it binds to streptavidin resulting in III*.

Figure 9C:
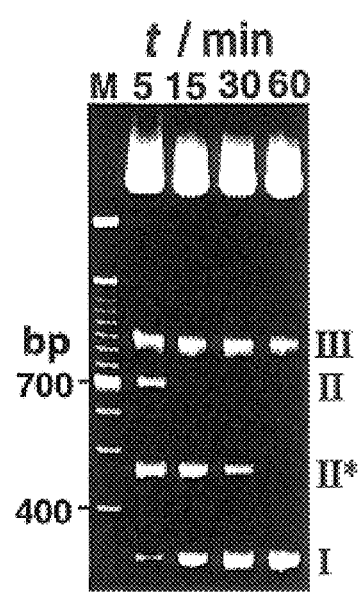
FIG. 9*c* is an image of a gel containing experimental data.

FIG. 9c shows the effect of heating a mixture of II and III at 65° C. for up to one hour. It is apparent that complex II disappears resulting in complex II* (i.e. II bound with a single PNA opener), and complex I due to loss of PNA openers. Complex III remains intact and the high stability of III is consistent with a pseudorotaxane structure.

For assembly of the linked catenane, supercoiled pPL3 plasmid was used and the formation of catenated complex was performed analogous to the formation of III described above. The resulting material was then cut with PvuII endonuclease after the ligation reaction a portion was retained and a portion was treated with exonuclease VII (USB, Cleveland Ohio). The exonucleaseVII treatment was performed in 1×ligation buffer with addition of 1 μL of exoVII (10 units), and incubation for 1 h at 37° C.

Figure 10A:
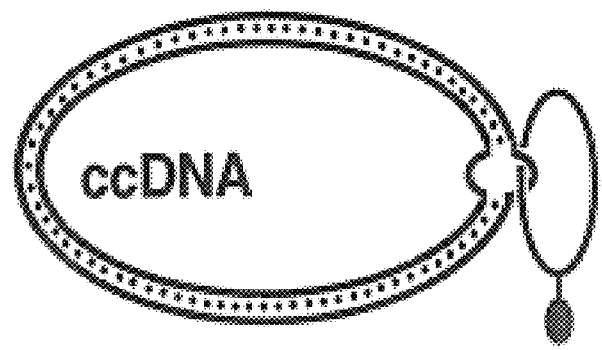
FIG. 10*a* is an illustration of an "Earring"complex.
Figure 10B:
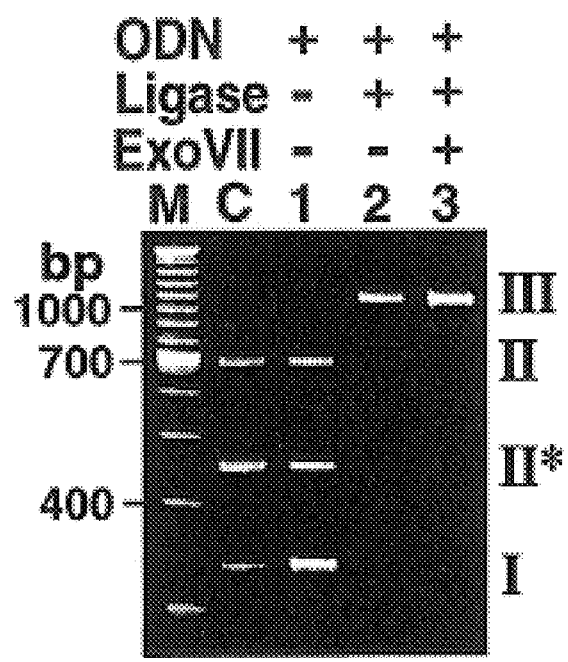
FIG. 10*b* is an image of a gel containing experimental data.

FIG. 10, lanes M and C are a size ladder and a control, respectively. Lanes 1–3 demonstrate that both ODN 4 and ligase are needed to form III and that III is stable to digestion by Exo VII, a single strand-specific exonuclease. The results are consistent with the formation of the catenane.

Example 4: Rolling The Earring

For this example, the Earring was constructed using a different plasmid and the general methods described in Example 3. Amplification reactions, as shown in FIGS. 11A & B, of both an Earring complex (template A) and a closed circular oligonucleotide (template B) were prepared with the oligonucleotide:

5'-CTGGAGGAGATTTTGTGGTATCGATTCGTCTCTTGAGGAAGCTA-3'    (Seq. ID No. 16)

and the oligonucleotide primer:

5'-GACGAATCGATACCAC-3'    Seq. ID 17

In the initial primer annealing step, 2 μl of ~0.1 μM template (A or B), 2 μl of 10 μM primer, 2 μl of Sequenase reaction buffer (5×concentrate; 200 mM Tris-HCl, pH 7.5, 100 mM MgCl$_2$, 250 mM NaCl) and 4 μl H$_2$O were incubated at 37° C. for 0.5 h. Some samples were then treated with exonuclease VII as described in Example 3. Then, 1 μl of 0.1 M DTT, 0.8 μl of 25 mM dNTP mix (dATP+dGTP+dCTP+dTTP; 25 mM each), 0.5 μl single-stranded binding protein (SSB, 2.2 μg/μl), 5.7 ηl H$_2$O, and 2 μl T 7 Sequenase version 2.0 DNA polymerase (3.25 units) were added to the annealed template-primer. The signal amplification reaction was performed for 3 h at 37° C. The reaction was terminated by addition of 12 μl Stop Solution (95% formamide, 20 mM EDTA, 0.05% bromophenol blue, 0.05% xylene cyanol FF). The samples were heated for 5 min at 80° C., chilled on ice, and loaded on 8% denaturing polyacrylamide gel. After electrophoresis at 300V for 3 h at room temperature, the gel is stained with SYBR Green II dye (Molecular Probes), and visualized by scanning with a CCD camera.

FIG. 11C shows the results of the experiments which demonstrate amplification of both the Earring (Panel A) and the closed circular template (Panel B). As in Example 3, pretreatment with exonuclease VII indicates that the stable Earring complex has formed and is the template for the amplification observed in Panel A.

EQUIVALENTS

While this invention has been particularly shown and described with references to preferred embodiments thereof, it will be understood by those of ordinary skill in the art that various changes in form and details may be made therein without departing from the spirit and scope of the invention as defined by the appended claims. Those skilled in the art will be able to ascertain, using no more than routine experimentation, many equivalents to the specific embodiments of the invention described herein. Such equivalents are intended to be encompassed in the scope of the claims.

We claim:

1. A composition comprising:
   a) double stranded nucleic acid having at least one homopurine site;
   b) one or more PNA oligomers that hybridize to one or more homopurine sites to thereby create an extended open region inside the double stranded nucleic acid;
   c) a nucleobase primer hybridized to the extended open region of the double stranded nucleic acid.

2. The composition of claim 1, wherein the one or more PNA oligomers that hybridize to the one or more homopurine sites are bis-PNAs.

3. The composition of claim 2, wherein each of the bis-PNAs comprise two polypyrimidine segments of five or greater PNA subunits in length and the homopurine sites of the double stranded nucleic acid are separated by between three to ten nucleotides.

4. The composition of claim 1, wherein the nucleobase primer is selected from the group consisting of an oligoribonucleotide, an oligodeoxynucleotide, an appropriately modified peptide nucleic acid, an appropriately modified linked polymer and an appropriately modified chimera.

5. The composition of claim 1, wherein the nucleobase primer hybridizes to the extended open region to form a double stranded hybrid.

6. The composition of claim 1, wherein the two or more homopurine sites are on different strands of the double stranded nucleic acid.

7. The composition of claim 1, wherein the double stranded nucleic acid comprises two or more homopurine sites.

8. The composition of claim 7, wherein the two or more homopurine sites are on the same strand of the double stranded nucleic acid and are separated by between zero and eleven nucleotides.

9. The composition of claim 8, wherein the nucleobase primer hybridizes to the strand of the nucleic acid that is opposite to the strand to which the two or more PNA oligomers hybridize.

10. The composition of claim 9, wherein bis-PNAs hybridize to the two or more homopurine sites.

11. A method for hybridizing a nucleobase primer to one strand of a double stranded nucleic acid; said method comprising:
    a) choosing a double stranded nucleic acid having at least one homopurine site;
    b) hybridizing one or more PNA oligomers to the one or more homopurine sites to thereby create an extended open region inside the double stranded nucleic acid; and
    c) hybridizing a nucleobase primer to the extended open region of the double stranded nucleic acid.

12. The method of claim 11, wherein two bis-PNAs hybridize to two homopurine sites which are separated by between zero to eleven nucleotides.

13. The method of claim 12, wherein each of the two bis-PNAs comprise two polypyrimidine segments of five or greater PNA subunits in length.

14. The method of claim 11, further comprising:
   d) initiating primer extension with a polymerase under suitable Sanger sequencing conditions to thereby generate Sanger sequencing ladders from the double stranded nucleic acid template.

15. The method of claim 14, wherein the polymerase is selected from the group consisting of Klenow DNA polymerase, T7 DNA polymerase, Sequenase, DNA polymerase 1 and phi 29.

16. The method of claim 14, further comprising:
   e) determining the sequence of the double stranded nucleic acid by analysis of the Sanger sequence ladder.

17. The method of claim 14, wherein the Sanger sequence ladder is generated in the presence of large excesses of other duplex nucleic acid.

18. The method of claim 16, wherein the Sanger sequence ladder is analyzed using an electrophoretic separation.

19. The method of claim 16, wherein the nucleobase primer is labeled and thereby generates a labeled Sanger sequence ladder that is analyzed.

20. The method of claim 19, wherein the label is selected from the group consisting of a hapten, an enzyme, a fluorophore, a chromophore, a chemiluminescent compound and a radioisotope.

21. The method of claim 20, further comprising
   f) choosing a new complex forming site having one or more homopurine sites;
   g) hybridizing one or more PNA oligomers to the one or more homopurine sites to thereby create an extended open region inside the double stranded nucleic acid;
   h) hybridizing a primer to the extended open region of the double stranded nucleic acid template; and
   i) repeating steps (d) and (e) of claims 14 and 16, respectively, to thereby generate the sequence of the double stranded nucleic acid template.

22. The method of claim 21, wherein the sequence information is downstream from the original complex forming site.

23. The method of claim 21, further comprising repeating the method until the sequence of the entire double stranded nucleic acid is determined.

24. The method of claim 21, wherein the sequence information is upstream from the original complex forming site.

* * * * *